United States Patent [19]
Tomcufcik et al.

[11] Patent Number: 5,877,196
[45] Date of Patent: Mar. 2, 1999

[54] N-[4-(IMIDAZOLYL OR PYRAZOLYL)PHENYL(OXY, SULFINYL, SULFENYL OR SULFONYL)ALKYL]CARBOXAMIDES, SULFONAMIDES OR PHOSPHORAMIDES HAVING ANTIARRHYTHMIC PROPERTIES

[75] Inventors: Andrew Stephen Tomcufcik, Old Tappan; Joseph William Hinson, Princeton, both of N.J.

[73] Assignee: American Cyanamid Company, Madison, N.J.

[21] Appl. No.: 800,313

[22] Filed: Feb. 14, 1997

Related U.S. Application Data

[60] Provisional application No. 60/012,416 Feb. 28, 1996.
[51] Int. Cl.$^6$ .................. A61K 31/415; A61K 31/40; C07D 233/64; C07D 207/32
[52] U.S. Cl. .................. 514/397; 514/399; 514/427; 518/341.1; 518/341.5; 518/342.1; 518/342.5; 518/343.5; 518/375.1; 518/376.1; 518/377.1; 518/575
[58] Field of Search .................. 514/397, 399, 514/427; 548/343.5, 341.1, 341.5, 342.1, 342.5, 375.1, 376.1, 377.1

[56] References Cited

U.S. PATENT DOCUMENTS 5,545,651  8/1996  Duncia et al. .................. 514/381

FOREIGN PATENT DOCUMENTS

| 0290377 | 11/1988 | European Pat. Off. ............ 548/343.5 |
| 0306440 | 3/1989 | European Pat. Off. ............ 548/343.5 |
| WO9529163 | 2/1995 | WIPO .................. C07D 233/58 |

*Primary Examiner*—Yogendra N. Gupta
*Attorney, Agent, or Firm*—R. F. Boswell

[57] ABSTRACT

The present invention relates to substituted ω-[phenoxy, phenylthio, phenylsulfinyl, phenylsulfonyl] [alkyl, alkenyl or alkynyl]amine carboxamides, sulfonamides and phosphonylamides which are useful as antiarrhythmic agents.

9 Claims, No Drawings

N-[4-(IMIDAZOLYL OR PYRAZOLYL) PHENYL(OXY, SULFINYL, SULFENYL OR SULFONYL)ALKYL]CARBOXAMIDES, SULFONAMIDES OR PHOSPHORAMIDES HAVING ANTIARRHYTHMIC PROPERTIES

This application claims priority to provisional application number 60/012416, filed Feb. 28, 1996

BACKGROUND OF THE INVENTION

1. Field of the Invention

The present invention relates to new substituted ω [phenoxy, phenylthio, phenylsulfinyl, phenylsulfonyl] [alkyl, alkenyl or alkynyl]amine carboxamides, sulfonamides and phosphonylamides which are useful as antiarrhythmic agents.

2. Background of the Invention

Antiarrhythmic agents are classified in one of four categories, sodium channel blockers (Class I), calcium channel blockers (Class II), potassium channel blockers (Class III) and β-adrenergic blockers (Class IV) based upon their ability to exhibit clearly definable pharmacological actions. Compounds contained in the present invention produce a homogenous prolongation of repolanzation and refractoriness which is indicative of Class III antiarrhythmic activity. The electrophysical mechanism underlying the prolongation of repolarization is known to be the blockade of currents through cardiac potassium channels. In contrast, Class I antiarrhythmic agents mediate their pharmacological effect through sodium channel blockade. In canine Purkinje fibers and papillary muscle preparations, the Class III antiarrhythmic action of quinidine is manifested by the prolongation of action potential duration (APD). The prolongation of the APD and the effective refractory period (ERP) has also been shown with other Class III antiarrhythmic agents such as d-sotalol (N-[4-[1-hydroxy-2-[(1-methylethyl)amino]ethyl]phenyl]methanesulfonamide), dofetilide (4'-(2-[methyl[4-(methylsulphonylamino)phenethyl]amino]ethoxy)methanesulphonanilide), and E-4031 (1-[2-(2-methylpyridin-6-yl)ethyl]-4-(4-methanesulfonylaminobenzoyl)-piperidine) which have shown pharmacological effects in clinical studies. The increase in APD in cardiac muscle has thus become an in vitro standard measure for putative Class III antiarrhythmic agents.

Class III antiarrhythmic activity is established as a viable therapeutic strategy for the management of ventricular arthythmias and the prevention of sudden cardiac death. Some recent reviews of Class III agents include: Gibson and Kersten, Drug Dev. Res., 1990, 19: 173–185; Carmeliet, Fundam. Clin. Pharniacol. 1993, 7: 19–28; Harrison and Bottorff, Advances in Pharmacology, 1992, 23: 179–215; Cimini and Gibson, Ann. Reports in Medicinal Chem. 1992, 27: 89–98.

Racemic sotalol is a structural prototype antiarrhythmic drug whose pharmacological activity stems from the blockade of the delayed rectifier subclass of potassium channels. Sotalol is a phenethanolamine derivative containing a methylsulfonamide moiety. Structural variations of this compound in which either chain extension by carbon or oxygen atoms or the addition of a second aryl moiety such as 4-phenoxyimidazole, have been achieved. However, the presence of a basic amine moiety within the original phenethyl chain has been retained. A general pharmacophore model for this class of compounds is defined and a generalized structure is proposed (Prog. Med. Chem. 1992, 29, 65) linking the structural variations; where Q is an electron withdrawing group, A is a one to four atom link between the aryl group and the nitrogen atom and the $R_1$ and $R_2$ substituents are selected from hydrogen, alkyl, arylalkyl or heteroarylalkyl groups.

The current invention is a departure from general Structure I, in that a carbonyl, sulfonyl or phosphoryl group is attached to the nitrogen (NH) atom. The current substituents change the physical chemical characteristics of the nitrogen atom (and therefore the pharmacophore) from one which is basic as in Structure I to one that has either neutral or acidic properties. This novel departure from the general pharmacophore defines a series of compounds which possess significant activity in the action potential prolongation procedure indicative of antiarrhythmic activity.

SUMMARY OF THE INVENTION

This invention relates to new derivatives selected from those of general formula I:

FORMULA I wherein $R_1$ is $-NO_2$, $-NH_2$, $-CN$, $-CSNH_2$ $R^3$ is $C_1$–$C_3$ straight chain alkyl;

X is O, S, SO or $SO_2$;

D is n is an integer from 3 to 10;
k is an integer from 1 to 4;
m is an integer from 1 to 4;

Y is

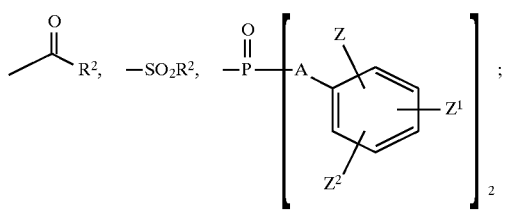

$R^2$ is

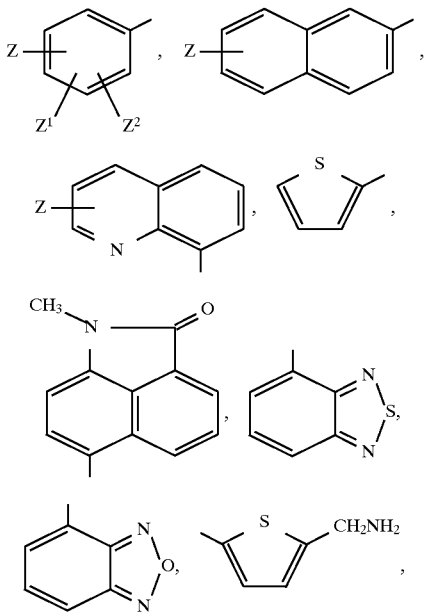

-continued

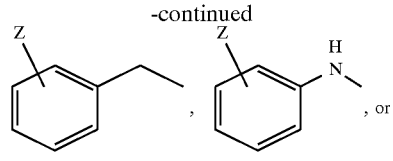, or $C_1$–$C_8$ alkyl, straight or branched

Z, $Z^1$ and $Z^2$ are independently selected from H, $C_1$–$C_4$ straight or branched alkyl, —$CF_3$, —$NO_2$, —$NHCOR^3$, —$OR^4$, —CN, Cl, Br, F, or I; $R^4$ is $C_1$–$C_4$ straight or branched alkyl; and A is oxygen or a bond; or a pharmaceutically acceptable salt thereof.

A pharmaceutically acceptable salt is an addition salt formed between an invention compound having a basic nitrogen and a pharmaceutically acceptable acid such as one of the inorganic acids hydrochloric, hydrobromic, sulfuric, or phosphoric acid, or an organic acid such as acetic, citric, maleic, fumaric, tartaric, succinic, methanesulfonic, or benzoic acid Within the group of compounds defined by Formula I, the most preferred compounds are those wherein $R^1$ is

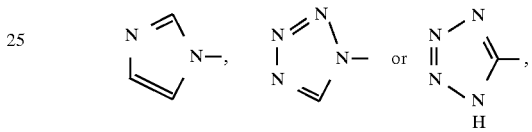

X is O and Y is $SO_2R^2$.

DETAILED DESCRIPTION OF THE INVENTION

The novel compounds of the present invention may be readily prepared in accordance with the following reaction schemes. Unless stated otherwise, all variable values are as previously defined.

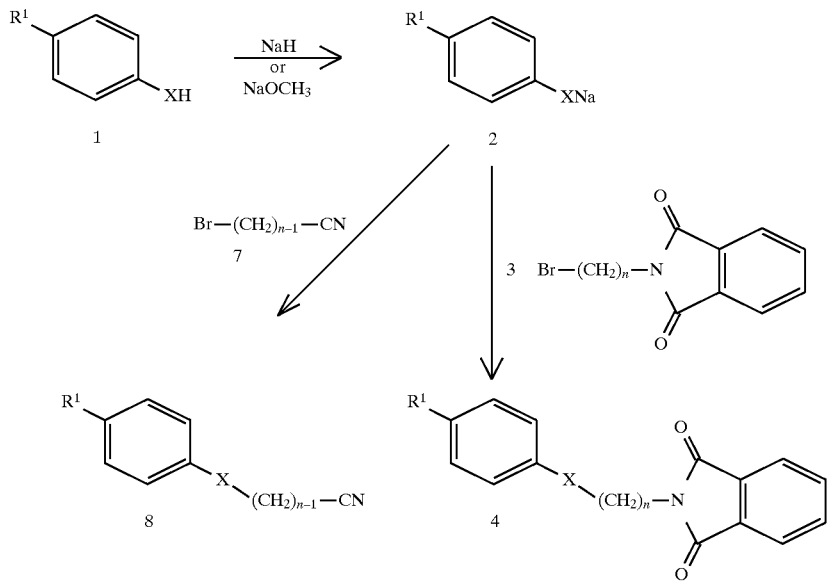

-continued
SCHEME I

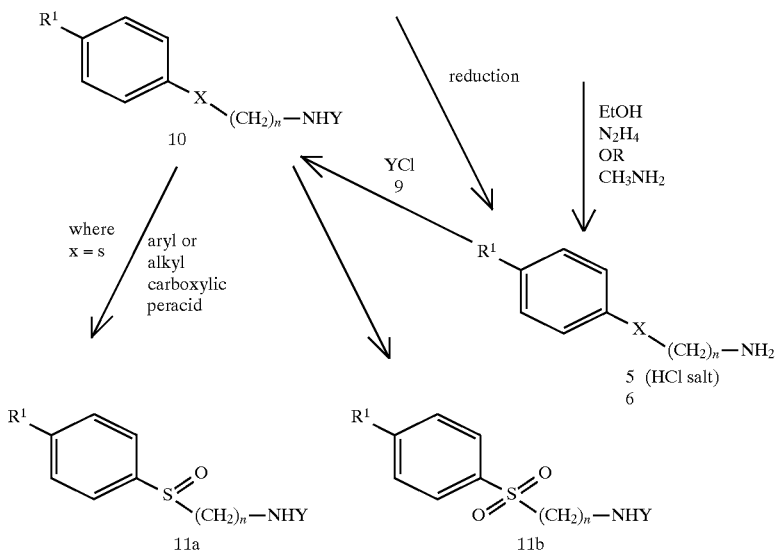

The compounds of formula I wherein D is —(CH$_2$)$_n$— may be prepared as described in Scheme I by dissolving a base such as sodium methoxide in a lower alkanol solvent and adding 1, or dissolving 1 in N,N-dimethylformamide and treating with sodium hydride to give 2. Reaction of 2 with the 2-(ω-bromoalkyl) derivative of 1H-isoindole-1,3 (2H)-dione 3, in a lower alkanol solvent followed by stirring from room temperature to the reflux temperature of the solvent for 12–16 hours gives intermediate 4. The product is isolated by cooling, collecting the solid, washing the solid with water and drying. Alternatively, reaction of 2 with 3 in N,N-dimethylformamide at or between room temperature and 95° C. on a steam bath gives 4 which is isolated by dilution with 5–10 volumes of water and collecting the product by filtration or by evaporating the N,N-dimethylformamide at reduced pressure and collecting the residue by filtration. Conversion of 4 to the free amine 6 or amine salts 5 is conducted by dissolving or suspending 4 in refluxing ethanol containing either hydrazine or monomethylamine for 12–18 hours, cooling and collecting the insoluble precipitate. The precipitate is washed with 2–5 equivalents of 1N HCl and the filtrate saved. The ethanol filtrate is concentrated to dryness and the residue is suspended 1N aqueous HCl solution. Insolubles are removed by filtration. The combined 1N HCl solutions are evaporated to give the HCl salt 5. Alternately, the filtrate can be rendered alkaline with NaOH, cooled to 0° C. and the free base 6 is collected by filtration. Additionally, reaction of 2 with 7 where n is 3 to 10 using conditions similar to those used in the reaction of 2 and 3 affords 8. Reduction of 8 using either hydrogen and a metal catalyst such as 10% palladium-on-carbon or a complex metal hydride such as lithium aluminum hydride upon isolation gives 6.

The hydrochloride salt 5 is added to water and 2.5 equivalents of sodium hydroxide is added. Sulfonyl chloride 9 where Y is —SO$_2$R$^2$ is dissolved in an ether solvent such as diethyl ether and added dropwise to 6. After stirring for 2–16 hours the precipitate is collected, washed with water and ether, dried and crystallized to give 10, where Y is —SO$_2$R$^2$.

Alternatively, 6 is dissolved in pyridine and a slight molar excess of 9 is added where Y is —SO$_2$R$^2$. The reaction mixture is stirred at between room temperature and steam bath temperature for 8–16 hours. The pyridine is removed at reduced pressure and the residue is washed with water, dried and crystallized to give 10.

Additionally, 6 is dissolved in dichloromethane containing an excess of triethylamine or N,N-diisopropylethylamine followed by the addition of 9 where Y is —SO$_2$R$^2$. The reaction mixture is stirred at or between room temperature and the reflux temperature of the solvent for 2–18 hours. The solvent is concentrated at reduced pressure and the residue is washed with water, dried and crystallized to give 10 where Y is —SO$_2$R$^2$.

Additionally, 5 or 6 are reacted with 9 where Y is

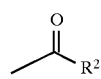

and to give 10 using the conditions to prepare 10 where Y is —SO$_2$R$^2$.

Furthermore, 5 or 6 are reacted with 9 where Y is

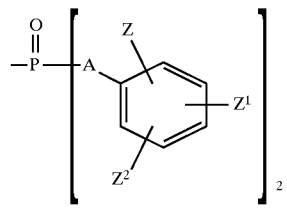

and A is oxygen or a bond to give 10 using the conditions described to prepare 10 where Y is —SO$_2$R$^2$.

Oxidation of 10 wherein X is S with one equivalent of an aryl or alkyl carboxylic peracid produces sulfoxide 11a or the sulfone 11b when an excess of the oxidizing reagent is present.

Scheme II
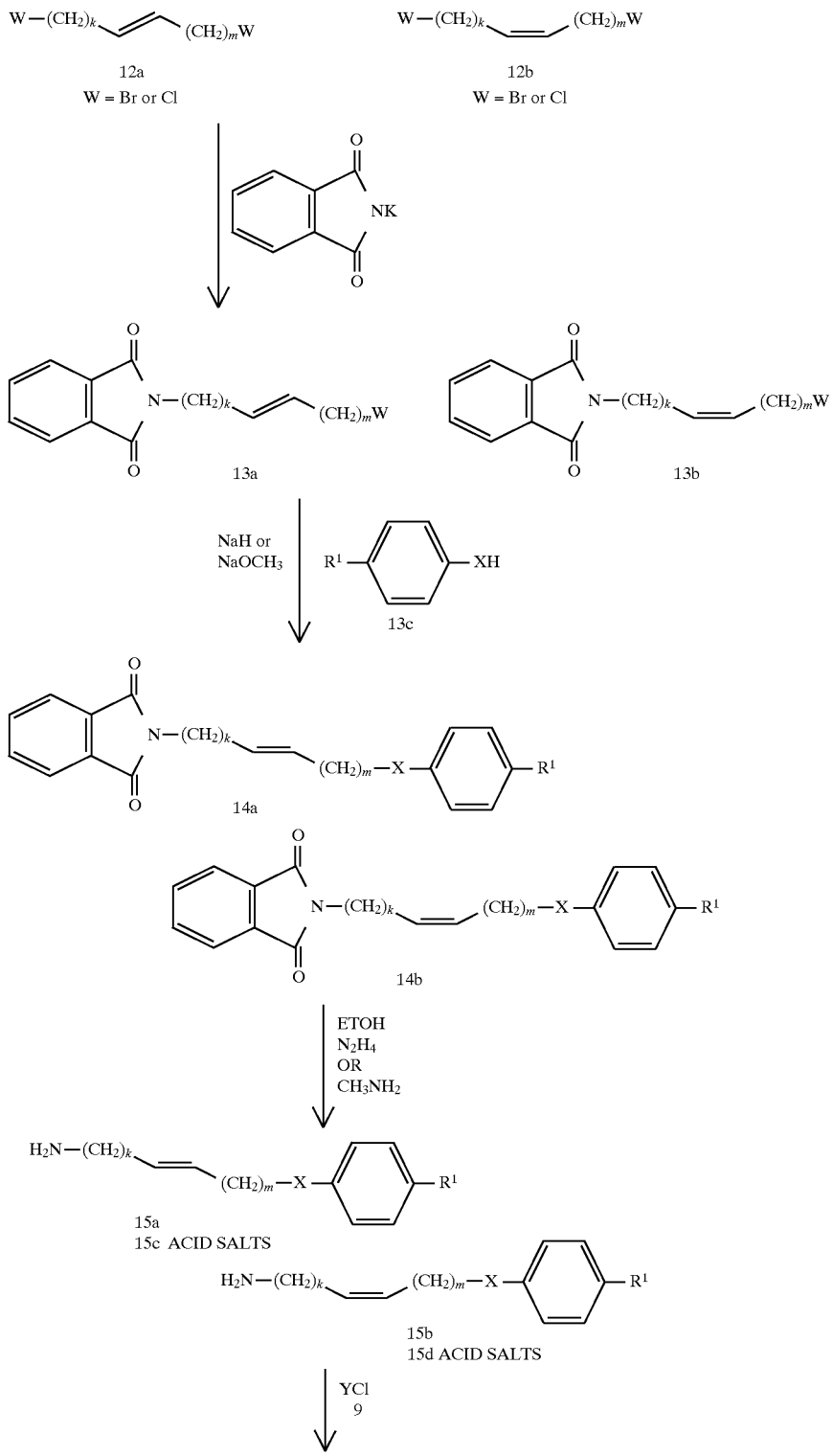

-continued
Scheme II

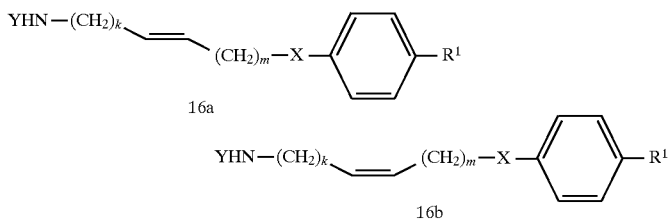

16a

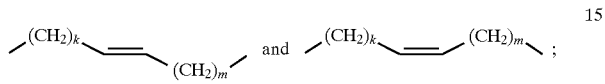

16b

The compounds of formula I wherein D is

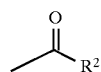  and  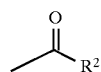 ;

are prepared as described in Scheme II by reaction of olefins 12a and 12b wherein W is Br or Cl with potassium salts of 1H-isoindole-1,3(2H)-dione in N,N-dimethylformamide at or between room temperature and the reflux temperature of the solvent for 12 to 16 hours to give intermediates 13a and 13b. Treatment of 13c with sodium hydride or sodium methoxide in N,N-dimethylformamide followed by reaction with 13a and 13b gives 14a and 14b. Reaction of 14a and 14b with hydrazine or monomethylamine in refluxing ethanol affords the free amines 15a and 15b or the acid addition salts such as hydrochloric, hydrobromic, hydroiodic, phosphoric, nitric or sulfate 15c and 15d. Sulfonyl chloride 9 where Y is —SO$_2$R$^2$ is dissolved in an ether solvent such as diethyl ether and added dropwise to 15a and 15b. After stirring for 2–16 hours the precipitate is collected, washed with water, ether, dried and crystallized to give 16a and 16b, where Y is —SO$_2$R$^2$.

Alternatively, 15c and 15d are dissolved in pyridine and a slight molar excess of 9 is added where Y is —SO$_2$R$^2$. The reaction mixture is stirred at or between room lo temperature and the reflux temperature of the solvent for 8–16 hours. The pyridine is removed at reduced pressure and the residue is washed with water, dried and crystallized to give 16a and 16b.

Additionally, 15c and 15d are dissolved in dichloromethane containing an excess of triethylamine or N,N-diisopropylethylamine followed by the addition of 9 where Y is —SOR$^2$ . The reaction mixture is stirred at or between room temperature and the reflux temperature of the solvent for 2–18 hours. The solvent is concentrated at reduced pressure and the residue is washed with water, dried and crystallized to give 16a and 16b where Y is —SO$_2$R$^2$.

Additionally, 15a, 15b, 15c, or 15d are reacted with 9 where Y is

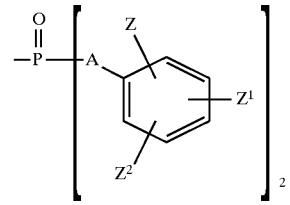

and R$^2$ is hereinbefore defined to give 16a and 16b using the conditions to prepare 10 where Y is —SO$_2$R$^2$.

Furthermore, 15a, 15b, 15c, or 15d are reacted with 9 where Y is

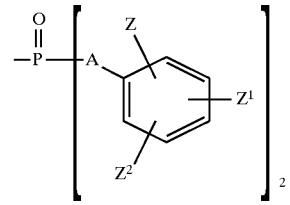

to give 16a and 16b using the conditions described to prepare 10 where Y is —SO$_2$R$^2$.

Scheme III

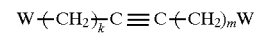

W= Br or Cl

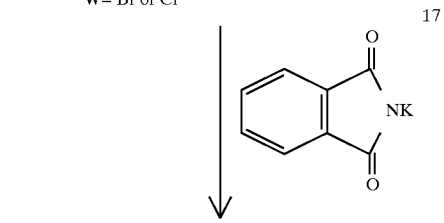

17

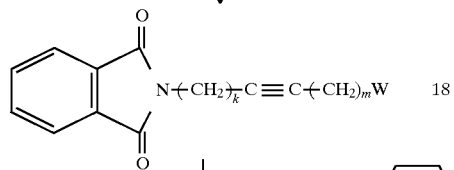

18

NaH or NaOCH$_3$   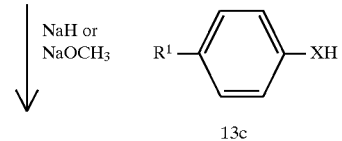

13c

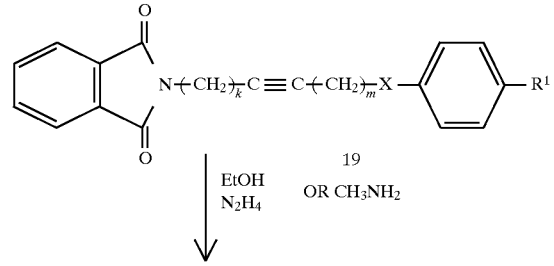

19

EtOH
N$_2$H$_4$   OR CH$_3$NH$_2$

-continued
Scheme III

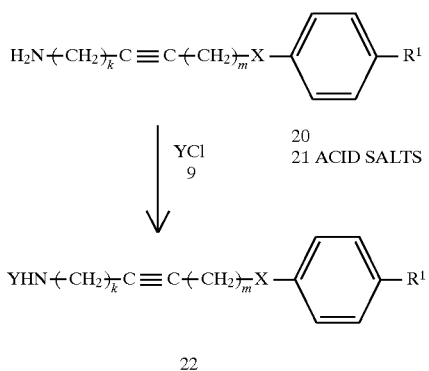

The compounds of formula I wherein D is

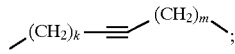

may be prepared as described in Scheme III by reaction of alkyne 17 wherein W is Br or Cl and k and m are hereinbefore defined with the potassium salt of 1H-isoindole-1,3-(2H)-dione in N,N-dimethylformamide at room temperature to give intermediate 18. Treatment of 13c with sodium hydride or sodium methoxide in N,N-dimethylformamide followed by reaction with 18 gives 19. Reaction of 19 with hydrazine or monomethylamine in refluxing ethanol affords the free amine 20 or the acid addition salt 21 such as hydrochloric, hydrobromic, hydroiodic, phosphoric, nitric or sulfate. Sulfonyl chloride 9 where Y is —$SOR^2$ is dissolved in ether and is added to 20. After stirring for 2–16 hours the precipitate is collected, washed with water, ether, dried and crystallized to give 22, where Y is —$SO_2R^2$.

Alternatively, 20 is dissolved in pyridine and a slight molar excess of 9 is added where Y is —$SO_2R^2$. The reaction mixture is stirred at or between room temperature and the reflux temperature of the solvent for 8–16 hours. The pyridine is removed at reduced pressure and the residue washed with water, dried and crystallized to give 22.

Additionally, 21 is dissolved in dichloromethane containing an excess of triethylamine or N,N-diisopropylethylamine followed by 9 where Y is —$SO_2R^2$. The reaction mixture is stirred at or between room temperature and the reflux temperature of the solvent for 2 to 18 hours. The solvent is concentrated at reduced pressure and the residue washed with water, dried and crystallized to give 22 where Y is —$SO_2R^2$.

Additionally, 20 or 21 are reacted with 9 where Y is

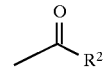

to give 22 using the conditions to prepare 10 where Y is —$SO_2R^2$.

Furthermore, 20 or 21 are reacted with 9 where Y is

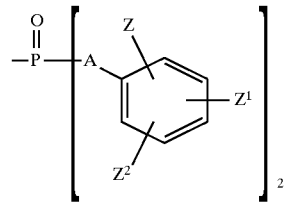

to give 22 using the conditions described to prepare 10 where Y is —$SO_2R^2$.

SCHEME IV

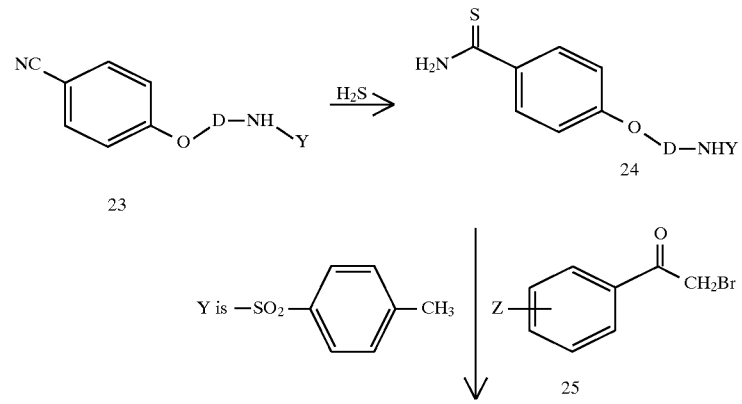

-continued
SCHEME IV

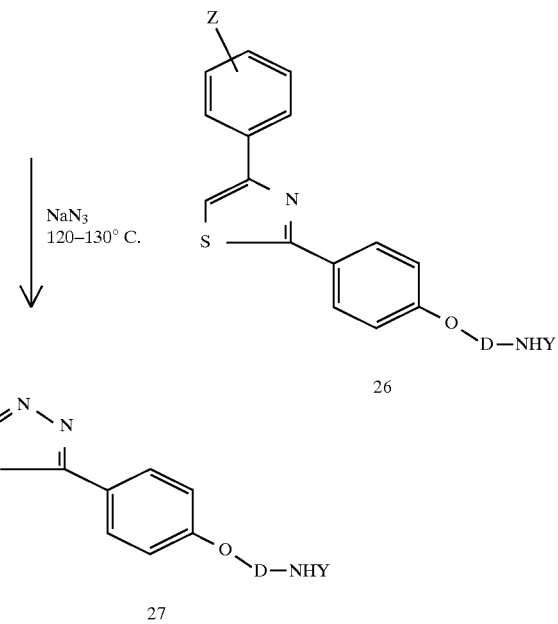

Referring to Scheme IV, sulfonamide 23 prepared by Schemes I, II and III where Y

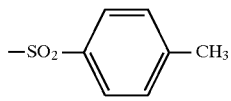

is reacted with hydrogen sulfide to give product 24. Reaction of 24 with α-bromoacetophenone 25 yields the thiazole 26.

Additionally, reaction of 23 where Y is

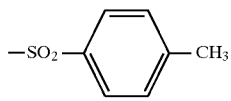

with sodium azide in N,N-dimethylformamide at 120°–130° C. in the presence of ammonium chloride gives tetrazole 27.

As shown in Scheme V, 28 prepared by Schemes I, II and III wherein is reacted with tris(formamido)methane and formamide at 160°–165° C. to give pyrimidine 29. Additionally, reaction of 28 with dimethylfornamide dimethylacetal gives eneaminone 30. Reaction of 30 is treated with hydrazine in refluxing ethanol to give pyrazole 31 or with formamidine to afford 29.

Reaction of 31 with 9 gives 32.

Cleavage of 29 by hydrazine or dimethylamine gives amine 33. Reaction of 33 with 9 gives 34.

Scheme V

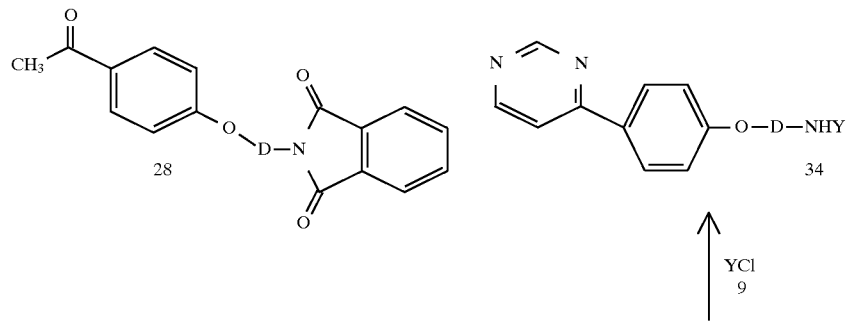

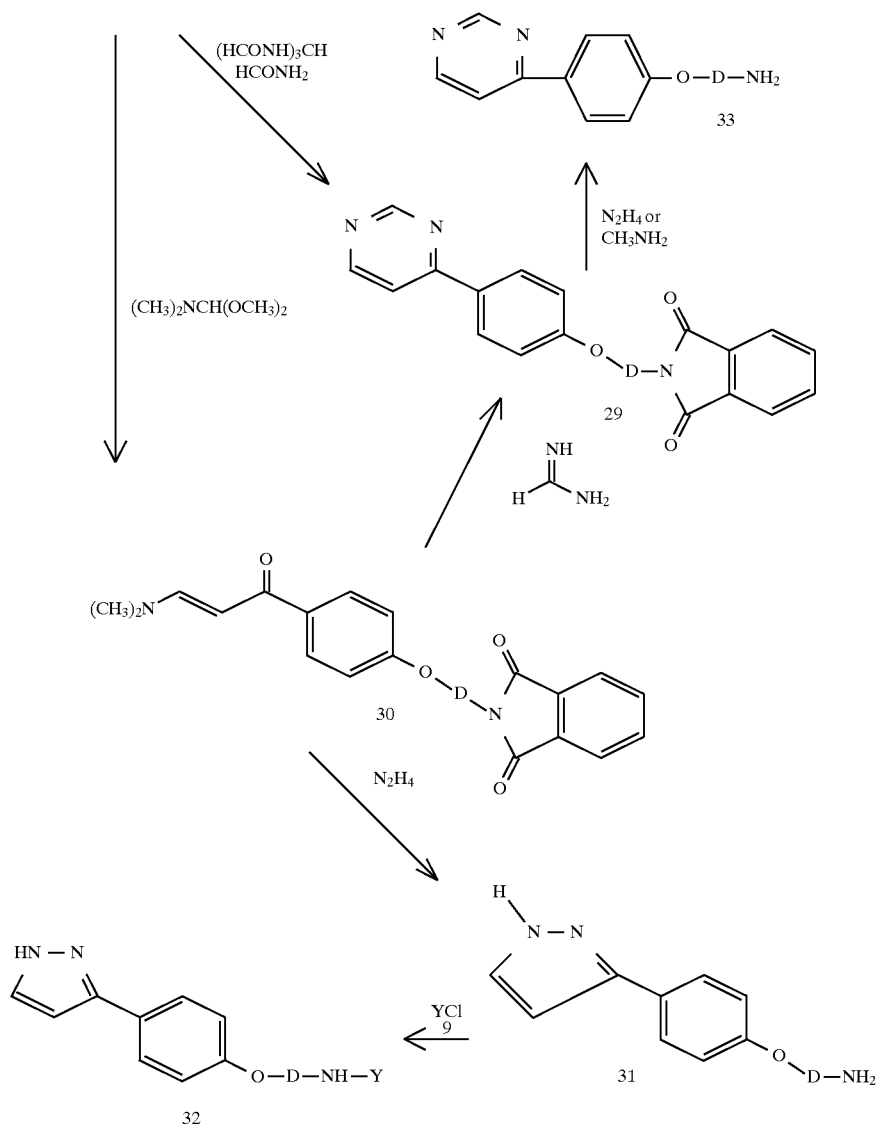
As shown in Scheme VI, benzenesulfonamide 35a, prepared by Schemes I, II and III, wherein Y is
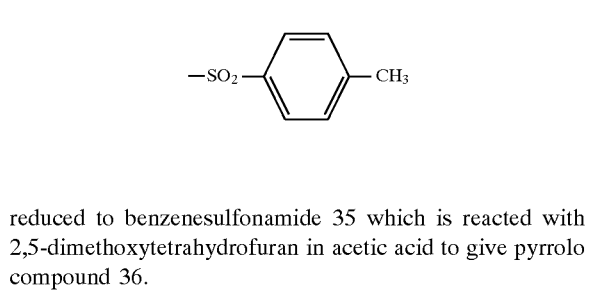
reduced to benzenesulfonamide 35 which is reacted with 2,5-dimethoxytetrahydrofuran in acetic acid to give pyrrolo compound 36.
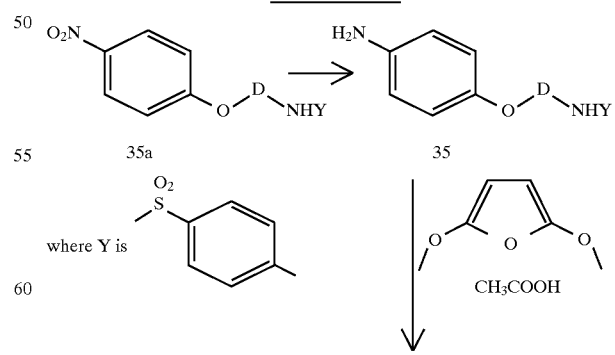

-continued
SCHEME VI

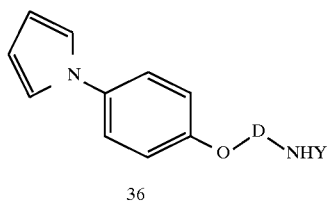

36

As shown in Scheme VII, 37a prepared by Schemes I, II and III is reduced to 37, which is then reacted with triethylorthoformate in the presence of sodium azide to give tetrazole 38.

SCHEME VII

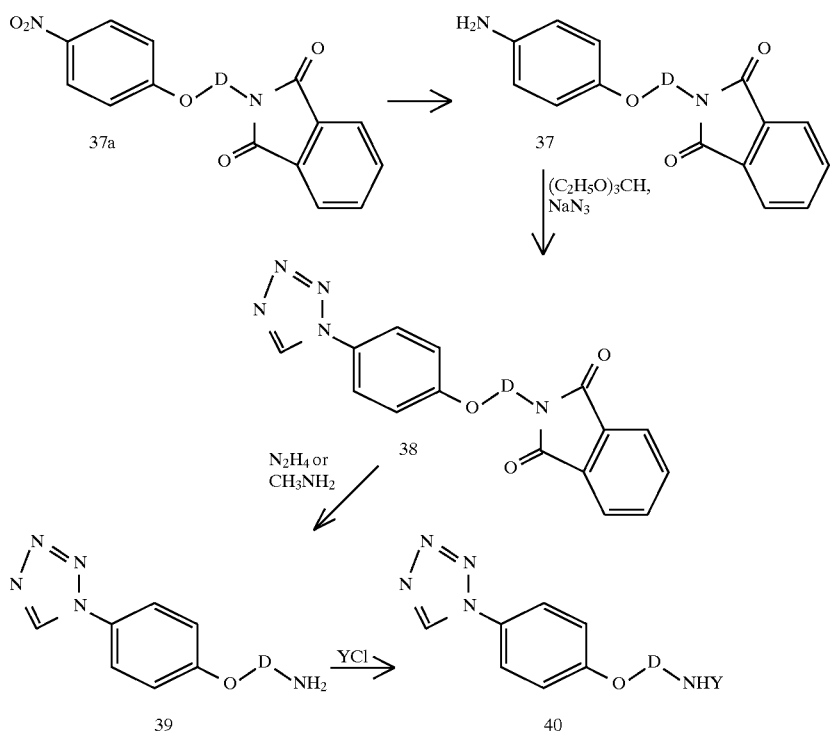

where Y is hereinbefore defined gives 40. Cleavage of 38 with hydrazine or methylamine gives amine 39. Reaction of 39 with YCl where Y is as defined previously gives a compound of formula 40.

The invention will be described in greater detail in conjunction with the following specific examples which are included for illustrative purposes. The reagents and intermediates used are either commercially available or can be synthesized by standard literature procedures by those skilled in the art of organic synthesis.

EXAMPLE 1

2-[4-[4-(1H-Imidazol-1-yl)phenyoxy]butyl]-1H-isoindole-1,3(2H)-dione

To a solution of 4.0 g of sodium methoxide in 100 ml of dimethylformamide is added 10.0 g of 4-(1H-(imidazol-1-yl)phenol. After a few minutes 18.2 g of 2-(4-bromobutyl)-1H-isoindole-1,3(2H)-dione is added, and the reaction mixture stirred and heated in the steam bath for 16 hours. Addition to two liters of cold water gives a precipitate which is collected, washed with one liter of cold water, and dried. Recrystallization from methylene chloride-hexane gives 14.7 g of a solid melting at 105°–107° C.

EXAMPLE 2

4-[4-(1H-Imidazol-1-yl)phenoxy]butaneamine

To a solution of 13.0 g of 2-[4-[4-1H-imidazol-1-yl)phenoxy]butyl]-1H-isoindole-1,3(2H)-dione (Example 1) in 250 ml of refluxing ethanol is added a 1.6 ml portion of anhydrous hydrazine. The mixture is stirred at reflux for 16 hours and taken to dryness in vacuo. The residue is mixed with 200 ml of ethanol and 25 ml of concentrated hydrochloric acid, and the mixture stirred at reflux for two hours. The hot reaction mixture is filtered and the precipitate is then washed with 100 ml of hot water. The combined filtrates are then taken to dryness in vacuo, leaving 8.4 g of the dihydrochloride salt of the title compound, mp 195°–200° C.

The title compound is obtained by dissolving the above dihydrochloride salt in $H_2O$, treating with excess 10N NaOH, and extraction with dichloromethane. After drying and removal of the dichloromethane, the base is obtained as a low melting solid.

EXAMPLE 3

4-(t-Butyl)-N-[4-[4-(1H-imidazol-1-yl)phenoxy]butyl]benzenesulfonamide

A solution of 3.0 g of 4-[4-(1H-imidazol-1-yl)phenoxy]butaneamine dihydrochloride (Example 2) is dissolved in 100 ml $H_2O$ and while stirring 3.5 ml of 10N NaOH, and then 2.6 g of 4-(t-butyl)benzenesulfonyl chloride in 100 ml of diethyl ether are added. The mixture is stirred at room temperature for 4 hours. The precipitate is collected, washed with 50 ml of water and 50 ml of diethyl ether, and air dried. Recrystallization from 50% aqueous ethanol gives 2.6 g of the title compound, m.p. 138°–140° C.

EXAMPLE 4

4-Bromo-N-[4-[4-(1H-imidazol-1-yl)phenoxy]butyl] benzenesulfonamide

Utilizing the procedure of Example 3, employing 3.0 g of 4-bromobenzenesulfonyl chloride, 0.6 g of the desired product is obtained as a white solid, m.p. 134°–136° C.

EXAMPLE 5

4-Chloro-[4-[4-(1H-imidazol-1-yl)phenoxy]butyl] benzenesulfonamide

The procedure of Example 3 is followed using 2.4 g of 4-chlorobenzenesulfonyl chloride. A yield of 1.6 g of the desired compound is obtained as a white solid, m.p. 122°–123° C.

EXAMPLE 6

N-[4-[4-(1H-Imidazol-1-yl)phenoxy]butyl]-2-naphthalenesulfonamide

The procedure of Example 3 is employed using 2.6 g of 2-naphthalenesulfonyl chloride. A yield of 1.9 g of the title compound is obtained as a white solid, m.p. 157°–158° C.

EXAMPLE 7

4-Methyl-N-[4-[4-(1H-imidazol-1-yl)phenoxy]butyl] benzenesulfonamide

Following the procedure of Example 3, using 2.2 g of 4-methylbenzenesulfonyl chloride, 0.8 g of the desired compound is obtained as a white solid, m.p. 96°–98° C.

EXAMPLE 8

4-Iodo-N-[4-[4-(1H-imidazol-1-yl)phenoxy]butyl] benzensulfonamide

Employing the procedure of Example 3, using 3.0 g of 4-iodobenzenesulfonyl chloride, 3.2 g the desired compound is obtained as a white solid, m.p. 150°–152° C.

EXAMPLE 9

N-[4-[4-(1H-Imidazol-1-yl)phenoxy]buty] benzenemethanesulfonamide

Following the procedure of Example 3, and using 2.1 g of benzenemethanesulfonyl chloride, 0.3 g the desired compound is obtained as a white solid, m. p. 123°–124° C.

EXAMPLE 10

N-[4-[4-(1H-Imidazol-1-yl)phenoxy]butyl]-8-quinolinesulfonamide

Utilizing the procedure of Example 3 and employing 2.4 g of 8-quinolinesulfonyl chloride, 1.8 g of the desired compound is obtained as a white solid, m.p. 131°–3° C.

EXAMPLE 11

N-[4-[4-(1H-Imidazol-1-yl)phenoxy]butyl]-2-thiophenesulfonamide

The title compound is prepared by the procedure of Example 3 and employing 2.0 g of 2-thiophenesulfonyl chloride; 1.9 g the desired compound is obtained as a solid, m.p. 121°–122° C.

EXAMPLE 12

N-[4-[4-(1H-Imidazol-1-yl)phenoxy]butyl]-1,2-dihydro-1-methyl-2-oxobenz[cd]indole-6-sulfonamide 1,2-Dihydro-1-methyl-2-oxobenz[cd]indole is dissolved in chlorosulfonic acid at room temperature. After eighteen hours at room temperature, the solution is added to crushed ice, precipitating the 6-sulfonyl chloride. This solid is collected, washed with water, and dried in vacuo at room temperature.

A solution of 2.8 g of the above sulfonyl chloride in 200 ml of dichloromethane is added to a stirred mixture of 3.0 g of 4-[4-(1H-imidazol-1-yl)-phenoxy]butaneamine dihydrochloride (Example 2) and 3.5 ml of 10N NaOH. After 6 hours, the dichloromethane layer is separated, washed with water, and dried over $Na_2SO_4$. Addition of an equal volume of hexane gives a yellow precipitate which is purified by recrystallization from ethanol; yield, 0.8 g; m.p. 177°–179° C.

EXAMPLE 13

2,5-Dichloro-N-[4-[4-(1H-imidazol-1-yl)phenoxy] butyl]benzenesulfonamide

The procedure of Example 3 is followed utilizing 2.6 g of 2,5-dichlorobenzenesulfonyl chloride. The desired compound is obtained as a white solid, m.p. 144°–146° C.; yield, 1.5 g.

EXAMPLE 14

4-Trifluoromethyl-N-[4-[4-(1H-imidazol-1-yl) phenoxy]butyl]benzenesulfonamide

The title compound is prepared by the procedure of Example 3, utilizing 0.01 mole of 4-trifluoromethylbenzenesulfonyl chloride. The desired compound is obtained as a solid, 119°–120° C; yield, 1.0 g.

EXAMPLE 15

4-Nitro-N-[4-[4-(1H-imidazol-1-yl)phenoxy]butyl] benzenesulfonamide

The title compound is prepared by the method of Example 3 utilizing 2.4 g of 4-nitrobenzenesulfonyl chloride. The desired compound is obtained in 0.5 g yield as a solid m.p. 156°–157° C.

EXAMPLE 16

4-Acetamido-N-[4-[4-(1H-imidazol-1-yl)phenoxy] butyl]benzenesulfonamide

The title product is prepared by the procedure of Example 3, utilizing 4-acetamidobenzenesulfonyl chloride. The desired product is obtained as a solid, m.p. 101°–103° C.; yield, 1.9 g.

EXAMPLE 17

4-Methoxy-[4-[4-(1H-imidazol-1-yl)phenoxy]butyl] benzenesulfonamide

The title compound is prepared by the procedure of Example 3, utilizing 0.011 mole of 4-methoxybenzenesulfonyl chloride. The desired product is obtained as a solid, m.p. 106°–107° C.; yield, 1.6 g.

EXAMPLE 18

N-[4-[4-(1H-Imidazol-1-yl)phenoxy]butyl]-1-octanesulfonamide

The procedure of Example 3 is followed, utilizing 2.3 g of octanesulfonyl chloride. The desired compound is obtained as a solid, m.p. 99°–100° C.; yield, 2.0 g.

EXAMPLE 19

2,4,6-Trimethyl-N-[4-[4-(1H-imidazol-1-yl)phenoxy]butyl]benzenesulfonamide

The title compound is prepared by the procedure of Example 3, utilizing 2.4 g of 2,4,6-trimethylbenzenesulfonyl chloride. The desired compound is collected as a solid, m.p. 130°–131° C.; yield, 0.8 g

EXAMPLE 20

N-[4-[4-(1H-Imidazol-1-yl)phenoxy]butyl]-2,1,3-benzothiadiazole-4-sulfonamide

The title compound is prepared by the procedure of Example 3, utilizing 2.6 g of 2,1,3-benzothiadiazole-4-sulfonyl chloride. The desired compound is obtained as a solid, m.p. 112°–114° C.; yield, 0.8 g.

EXAMPLE 21

4-Cyano-N-[4-[4-(1H-imidazol-1-yl)phenoxy]butyl]benzenesulfonamide

The title compound is prepared by the procedure of Example 3, utilizing 2.2 g of 4-cyanobenzenesulfonyl chloride. The desired compound is obtained as a solid, m.p. 148°–149° C.; yield 2.0 g.

EXAMPLE 22

4-Butoxy-N-[4-[4-(1H-imidazol-1-yl)phenoxy]butyl]benzenesulfonamide

The compound is prepared by the method of Example 3 using 2.8 g of 4-butoxybenzenesulfonyl chloride. The desired compound is collected as a solid, m.p. 103°–105° C.; yield, 1.5 g.

EXAMPLE 23

N-[4-[4-(1H-Imidazol-1-yl)phenoxy]butyl]benzenesulfonamide

The title compound is prepared by the procedure of Example 3, utilizing 1.4 ml of benzenesulfonyl chloride. The desired compound is collected as a solid, m.p. 110°–111° C.; yield 1.5 g.

EXAMPLE 24

N-[4-[4-(1H-Imidazol-1-yl)phenoxy]butyl]-2,1,3-benzoxadiazole-4-sulfonamide

The title compound is prepared by the procedure of Example 3, utilizing 2.0 g of 2,1,3-benzoxadiazole-4-sulfonyl chloride. The desired compound is collected as a white solid, m.p. 125°–126° C.; yield, 1.0 g.

EXAMPLE 25

5-Aminomethyl-N-[4-[4-(1H-imidazol-1-yl)phenoxy]butyl]-2-thiophenesulfonamide

A solution of 3.0 g of 5-benzoylaminomethyl-2-thiophenesulfonyl chloride, in 100 ml of dichloromethane, is added to a stirred mixture of 3.0 g of 4-[4-(1H-imidazol-1-yl)phenoxy]butaneamine dihydrochloride (Example 2) and 3.5 ml of 10N NaOH in 100 ml of water. The mixture is stirred at room temperature for 3 hours, a tacky precipitate being formed. The precipitate is mixed with 100 ml of concentrate HCl, and the mixture is stirred at reflux for 12 hours, solution taking place. The solution is taken to dryness in vacuo, and the dihydrochloride salt of the title compound was recrystallized from aqueous ethanol, m.p. 230°–232° C. (dec.); yield, 0.5 g.

EXAMPLE 26

2-[5-[4-(1H-imidazol-1-yl)phenoxy]pentyl-1H-isoindole-1,3-(2H)-dione

The title compound is prepared essentially by the procedure of Example 1, 2-(5-bromopentyl)-1H-isoindole-1,3 (2H)-dione replacing the 4-bromobutyl intermediate. Recrystallization of the collected solid from dichloromethane-hexane gives the desired product m.p., 105°–106° C.

EXAMPLE 27

5-[4-(1H-imidazol-1-yl)phenoxy]pentaneamine

2-[5-[4-(1H-imidazol-1-yl)phenoxy]butyl]-1H-isoindole-1,3-(2H)-dione (Example 26) is cleaved by hydrazine in refluxing ethanol by the procedure of Example 2. The crude hydrochloride salt is dissolved in 20 parts of water, made basic with 10N NaOH, and the mixture then extracted with 30 parts of dichloromethane. After drying with Na$_2$SO$_4$, the dichloromethane is removed in vacuo to give the desired compound as a clear oil, with the correct molecular weight as determined by mass spectrometry.

EXAMPLE 28

4-Bromo-N-[5-[4-(1H-imidazol-1-yl)phenoxy]pentyl]benzenesulfonamide

5-[4-(1H-imidazol-1-yl)phenoxy]pentaneamine (Example 27) is converted to the title compound by the procedure of Example 4, to give the desired compound as a solid, m.p. 137°–138° C.

EXAMPLE 29

N-[5-[4-(1H-Imidazol-1-yl)phenoxy]pentyl]hexanesulfonamide

The desired product is obtained by utilizing 5-[4-(1H-imidazol-1-yl)phenoxy]pentaneamine (Example 27) and hexanesulfonyl chloride by the procedure of Example 3, which gives the title compound as a solid.

EXAMPLE 30

(E)-2-[4-[4-(1H-Imidazol-1-yl)phenoxy]-2-buten-1-yl]-1H-isoindole-1,3(2H)-dione (E)-1,4-Dichloro-2-butene and potassium phthalimide are added to dimethylformamide, and the mixture stirred at room temperature for 18 hours. The reaction mixture is taken to dryness in vacuo. The residue is shaken with cold water, precipitating (E)-2-(4-chloro-2-buten-1-yl)-1H-isoindole-1,3(2H)-dione, which is purified by recrystallization from hexane; m.p. 100°–101 ° C.

A solution of 16.0 g of 4-(1H-imidazol-1-yl)phenol in 250 ml of dimethylformamide, is treated with 4.2 g of 60% NaH.

To the suspension of the sodium salt, 23.5 g of (E)-2-[4-chloro-2-buten-1-yl)-1H-isoindole-1,3(2H)-dione is added, and the reaction mixture stirred and heated on the steam bath for 16 hours. The dimethylformamide is removed in vacuo, and the residue stirred with 250 ml of water. The insolubles are collected, washed with water, and dried. Recrystallization from ethanol gives the desired product as a solid, m.p. 170°–171° C.

EXAMPLE 31

(E)-4-[4-(1H-Imidazol-1-yl)phenoxy]-2-buten-1-amine

A solution of 26.2 g of (E)2-[4-[4-(1H-imidazol-1-yl)phenoxy]-2-buten-1-yl]-1H-isoindole-1,3(2H)-dione (Example 30) in 1 liter of ethanol is treated with 5 ml of anhydrous hydrazine, and the mixture stirred at reflux for 18 hours. To the reaction mixture is added 25 ml of concentrated HCl and the mixture cooled to room temperature. The precipitate is collected and washed with 2 portions of 300 ml of water. The filtrate and aqueous washes are combined and taken to dryness in vacuo. The solid is treated with 25 ml of 10N NaOH, the mixture saturated with solid $K_2CO_3$, and then extracted with 500 ml of dichloro-methane. Removal of the dichloromethane in vacuo leaves a viscous oil that solidifies at room temperature. A portion is purified by recrystallization from hexane, and dried; m.p. 81°–83° C.; yield, 0.5 g.

EXAMPLE 32

(E)-4-Methyl-N-[4-[4-(1H-imidazol-1l-yl)phenoxyl-2-buten-1yl]benzenesulfonamide

A suspension of 3.4 g of (E)-4-[4-(1H-imidazol-1-yl)phenoxy]-2-butene-1-amine (Example 31) in 300 ml of diethylether and 5 ml of triethylamine is treated with a solution of 3.0 g of 4-methyltoluenesulfonyl chloride in 100 ml of diethyl ether. The mixture is stirred at room temperature for 12 hours, refluxed for two hours, and filtered hot. The precipitate is washed with 50 ml of $H_2O$ and 100 ml of ether, and air-dried. Recrystallization from ethanol gives the pure title compound, m.p. 140°–142° C.; yield 2.4 g.

EXAMPLE 33

2-[4-(4-Nitrophenoxy)butyl]-1H-isoindole-1,3 (2H)-dione

A solution of 14.0 g of 4-nitrophenol in 250 ml of dimethylformamide is treated with 6.0 g of sodium methoxide. After 15 minutes, 28.2 g of 2-(4-bromobutyl)-1H-isoindole-1,3(2H)-dione is added, and the mixture then stirred at room temperature for 16 hours. The reaction mixture is diluted with 1500 ml of cold water, the precipitated solid collected, washed with water, and dried. Recrystallization from ethanol gives the desired compound, m.p. 112°–114° C.

EXAMPLE 34

4-[4-Nitrophenoxy]butaneamine

A suspension of 62.6 g of 2-[4-(4-nitrophenoxy)butyl]-1H-isoindole-1,3(2H)-dione (Example 33) in one liter of ethanol is treated with 6.5 ml of hydrazine, and the mixture then stirred at reflux for 18 hours. After cooling to room temperature, the precipitate is collected, washed with 250 ml of hot 2.5N HCl, and 200 ml of hot $H_2O$. The combined acid and water washes are taken to dryness to obtain the hydrochloride salt of the title compound. Mass spectrometry shows the presence of the title compound. The compound is utilized directly without further purification.

EXAMPLE 35

4-Methyl-N-[4-(4-nitrophenoxy)butyl]benzenesulfonamide

A solution of 8.8 g of 4-(4-nitrophenoxy)-butaneamine hydrochloride (Example 34) in 200 ml of water is treated successively with 9 ml of 10N NaOH, and a solution of 7.5 g of 4-methylbenzenesulfonyl chloride in 200 ml of diethylether. The reaction is stirred at room temperature for 3 hours, the precipitate collected, washed with water and diethylether, and air dried. Recrystallization from 50% aqueous ethanol gives the desired product as a solid, m.p. 87°–88° C.; yield, 1.2 g.

EXAMPLE 36

4-Methyl-N-[4-(4-aminophenoxy)butyl]benzenesulfonamide 5.0 g of 4-methyl-N-[4-(4-nitrophenoxy)-butyl]benzenesulfonamide (Example 35) is dissolved in 500 ml of ethanol, 1.5 ml of anhydrous hydrazine and 500 mg of 10% palladium on carbon are added, and the mixture is then stirred under reflux for four hours. The reaction mixture is filtered hot. Cooling the filtrate to room temperature produces a precipitate, which is collected. The filtrate is reheated to boiling and utilized to re-extract the palladium-carbon residue, and after filtration, cooled to room temperature, the precipitate being collected. The process is repeated until no further precipitate is formed on cooling to room temperature. After drying at 60° in vacuo, the combined precipitates weigh 3.3 g; m.p. 176°–178° C.

EXAMPLE 37

2-[4-(4-Aminophenoxy)butyl]-1H-isoindole-1,3(2H)-dione

A suspension of 6.8 g of 2-[4-(4-nitro-phenoxy)butyl]-1H-isoindole-1,3(2H)-dione (Example 33) in 200 ml of ethanol is treated with 500 mg of 10% Pd on carbon, and reduced in a Parr hydrogenator. After filtration, concentration of the filtrate gives the desired product, m.p. 119°–121° C.; yield 4.3 g.

EXAMPLE 38

2-[4-[4-(1H-Tetrazol-1-yl)phenoxy]butyl]-1H-isoindole-1,3(2H)-dione

To a solution of 17.7 g of 2-[4-(4-amino-phenoxy)butyl]-1H-isoindole-1,3(2H)-dione (Example 37) in a mixture of 250 ml of acetic acid and 80 ml of triethylorthoformate is added 7.0 g of sodium azide and the mixture then stirred and heated on the steam bath for 4 hours. Concentration to dryness in vacuo leaves a residue that is triturated with 250 ml of water. The insolubles are collected, washed with water, and dried. Recrystallization from ethanol gives the title compound, m.p. 143°–145° C.

EXAMPLE 39

4-[4-(1H-Tetrazol-1-yl)phenoxy]butaneamine

A suspension of 19.4 g of 2-[4-[4-(1H-tetrazol-1-yl)phenoxy]butyl]-1H-isoindole-1,3(2H)-dione (Example 38)

in 400 ml boiling ethanol is treated with 3 ml of anhydrous hydrazine, and the mixture stirred at reflux for 16 hours. The precipitate is collected, washed with 200 ml of hot 1.5N HCl, and 50 ml of H$_2$O. The combined ethanol, hydrochloric acid, and water filtrates are taken to dryness in vacuo to give the hydrochloride salt of the title compound. A portion of the salt was recrystallized from hot ethanol, m.p. 197°–198° C. (dec.).

EXAMPLE 40

4-Bromo-N-[4-[4-(1H-tetrazol-1-yl)phenoxy]butyl]benzenesulfonamide

A solution of 2.7 g of 4-[4-(1H-tetrazol-1-yl)phenoxy]butaneamine hydrochloride (Example 39) in 100 ml of water is treated successively with 3.5 ml of 10N NaOH and a solution of 2.7 g of 4-bromobenzenesulfonyl chloride in 100 ml of diethyl ether. The mixture is stirred at room temperature for 1.5 hours, the precipitate collected, washed with diethyl ether and water, and air dried. Recrystallization from ethanol gives the pure compound, m.p. 109°–110° C.; yield, 1.6 g.

EXAMPLE 41

4-Methyl-N-[4-[4-(1H-tetrazol-1-yl)phenoxy]butyl]benzenesulfonamide

The subject compound is prepared essentially by the procedure of Example 40, 4-methylbenzenesulfonyl chloride replacing the 4-bromobenzenesulfonyl chloride. The desired compound is collected as a solid, m.p. 127°–128° C.

EXAMPLE 42

2-[4-(4-Acetylphenoxy)butyl]-1H-isoindole-1,3(2H)-dione

The subject compound is prepared essentially by the procedure of Example 33, 1-(4-hydroxyphenyl)-ethanone replacing the 4-nitrophenol. Recrystallization of the collected solid from ethanol gives the desired product, m.p. 112°–114° C.

EXAMPLE 43

1-[4-(4-Aminobutoxy)phenyl]ethanone

A suspension of 13.5 g of 2-[4-(4-acetyl-phenoxy)butyl]-1H-isoindole-1,3(2H)-dione in 500 ml of ethanol is treated with 1.4 ml of anhydrous hydrazine, and the mixture stirred at reflux for 9 hours. After cooling to room temperature, the precipitate is collected. Concentration of the filtrate gives the crude title compound, which is used directly for further synthesis.

EXAMPLE 44

1-[4-[4-(4-Bromobenzene-sulfonamido)butoxy]phenyl]ethanone

The desired product is prepared using the conditions of Example 40, using 1-[4-(4-aminobutoxy)phenylethanone in place of 4-[4-(1H-tetrazol-1-yl)-phenoxy]butaneamine; m.p. 129°–130° C.

EXAMPLE 45

2-[4-[4-(Pyrimidin-4-yl)phenoxy]butyl]-1H-isoindole-1,3(2H)-dione

A mixture of 10.0 g of 2-[4-(4-acetylphenoxy]-butyl]-1H-isoindole-1,3(2H)-dione (Example 42) 10.0 g of tris (formamido)methane, and 20 ml of formamide are combined and the mixture stirred and heated at 160°–165° C. for 8 hours. After dilution with 100 ml of water, the mixture is rendered basic with 10N NaOH, the precipitate collected, washed with water, and air dried. Recrystallization from ethanol gives the pure compound, m.p. 100°–102° C.; yield, 5.0 g.

EXAMPLE 46

4-[4-(Pyrimidin-4-yl)phenoxy]butaneamine

A suspension of 4.6 g of 2-[4-[4-(pyrimidin-4-yl)phenoxy]butyl]-1H-isoindole-1,3(2H)-dione (Example 45) in 200 ml of boiling ethanol is treated with 0.8 ml of anhydrous hydrazine, and the mixture then refluxed for 9 hours. The hot suspension is filtered. The precipitate is washed with 125 ml of 1.5N HCl. The combined HCl and ethanolic filtrates are taken to dryness in vacuo to obtain the hydrochloride salt of the title compound. Mass spectrometry shows the residue to be the tide compound and the salt is utilized for synthesis without further purification, m.p. 208°–210° C. (dec.).

EXAMPLE 47

4-Bromo-N-[4-[4-(pyrimidin-4-yl)phenoxy]butyl]benzenesulfonamide

The subject compound is prepared essentially by the procedure of Example 4, 4-[4-(pyrimidin-4-yl)phenoxy]butaneamine hydrochloride (Example 46) replacing the 4-[4-(1H-imidazol-1-yl)phenoxy]butaneamine hydrochloride. The desired compound is obtained as a solid after recrystallization from 50% aqueous ethanol, m.p. 131°–133° C.

EXAMPLE 48

(E)-2-[4-[4-[3-(dimethylamino)-1-oxo-2-propenyl]phenoxy]butyl]-1H-isoindole-1,3(2H)-dione A solution of 25 g of 2-[4-(4-acetylphenoxy)butyl]-1H-isoindole-1,3(2H)-dione (Example 42) and 25 ml of dimethylformamide dimethylacetal in 50 ml of dioxane is heated in the steam bath for 16 hours. The volatile components are removed in vacuo, a tacky reddish-brown solid being obtained. A portion is recrystallized from dichloromethane/hexane; m.p. 109°–111° C.

EXAMPLE 49

4-[4-(1H-Pyrazol-3-yl)phenoxy]butaneamine

A suspension of 21.2 g of (E)-2-[4-[4-[3-(dimethylamino)-1-oxo-2-propenyl]phenoxy]butyl]-1H-isoindole-1,3(2H)-dione (Example 48) in 300 ml of boiling ethanol is treated with 6 ml of anhydrous hydrazine. A suspension quickly develops, necessitating addition of 200 ml more ethanol to permit stirring. While stirring 35 ml of concentrated HCl is then added, the mixture refluxed a further hour, and filtered hot. The insolubles are washed with 200 ml of boiling water. The combined filtrates are taken to dryness in vacuo, leaving the hydrochloride salt of the title compound as shown by mass spectrometry. The product is utilized for synthesis without further purification.

EXAMPLE 50

4-Bromo-N-[4-[4-(1H-pyrazol-3-yl)phenoxy]butyl]benzenesulfonamide

The title compound is prepared essentially by the procedure of Example 40, 4-[4-(1H-pyrazol-3-yl)phenoxy]

butaneamine hydrochloride (Example 49) replacing the 4-[4-(1H-tetrazol-1-yl)phenoxy]butane amine hydrochloride. The resulting compound is recrystallized from 50% aqueous ethanol, m.p. 157°–158° C.

EXAMPLE 51

2-[4-(4-Cyanophenoxy)butyl]-1H-isoindole-1,3(2H)-dione

The title compound is prepared essentially by the procedure of Example 33, 4-hydroxybenzonitrile replacing the 4-nitrophenol. The resulting solid is collected, m.p. 129°–130° C.

EXAMPLE 52

4-(4-Aminobutoxy)benzonitrile

A suspension of 48.0 g of 2-[4-(4-cyano-phenoxy)butyl]-1H-isoindole-1,3(2H)-dione (Example 51) in one liter of refluxing ethanol is treated with 10 ml of anhydrous hydrazine. The mixture is stirred at reflux for 14 hours. After cooling to room temperature, the precipitate is filtered off and washed with 100 ml of ethanol. The ethanol filtrates are combined and taken to dryness in vacuo. The oil is dissolved in 100 ml of ethanol containing 15 ml of concentrated hydrochloric acid. Concentration of the solution in vacuo gives the crude hydrochloride salt of the tide compound, purified by recrystallization from ethanol; m.p. 144°–145° C.; yield, 7.2 g.

EXAMPLE 53

4-Methyl-N-[4-(4-cyanophenyloxy)butyl]benzenesulfonamide

A solution of 3.4 g of 4-(4-aminobutoxy)benzonitrile hydrochloride (Example 52) is in 100 ml of water is treated successively with 3.5 ml of 10N NaOH and 3.5 g of 4-methylphenylsulfonyl chloride in 100 ml of diethyl ether. The mixture is stirred at room temperature for two hours, a precipitate forming. The solid is collected, washed with water and diethyl ether, dried, and recrystallized from 50% aqueous ethanol; m.p. 107°–108° C.; yield, 3.5 g.

EXAMPLE 54

4-Methyl-N-[4-[4-(1H-tetrazol-5-yl)phenoxy]butyl]benzenesulfonamide

A mixture of 3.4 g of 4-methyl-N-[4-(4-cyanophenoxy)butyl]benzenesulfonamlde (Example 53), 1.3 g of sodium azide, 1.5 g of ammonium chloride, and 25 ml of dimethylformamide is stirred at 120°–130° C. (oil bath) for 16 hours. The reaction mixture is added to 200 ml of water and the resultant solution then acidified to pH 4–5 with acetic acid. The precipitate that forms is collected, washed with water, dried and recrystallized from boiling ethanol. Cooling gives the pure compound, m.p. 180°–182° C.; yield, 2.4 g.

EXAMPLE 55

4-Methyl-N-[4-(4-(thiocarbamylphenoxy)butyl]benzenesulfonanide

A solution of 3.5 g of 4-methyl-N-[4-(4-cyanophenoxy)butyl]benzenesulfonamide (Example 53) in a mixture of 30 ml of pyridine and 5 ml of triethylamine is gassed with a slow stream of hydrogen sulfide for 30 minutes and placed in a stoppered flask. After 7 days, the volatile components are removed in vacuo. The oily residue is recrystallized from 50% aqueous ethanol, yielding the pure compound as yellow crystals, m.p. 140°–141° C.; yield, 3.0 g.

EXAMPLE 56

N-Dimethylaminomethylidene-4-[(4-methyl]phenylsulfonamido)butyoxy]thiobenzamide 3.6 g of 4-methyl-N-[4-(4-thiocarbamyl-phenoxy)butyl]benzenesulfonamide is added to 30 ml of dimethylformamide dimethylacetal, and the mixture is stirred at room temperature for one hour. The precipitate is collected, washed with diethyl ether, and dried in vacuo at 40° C. The yield of title compound is 3.9 g; m.p. 115°–117° C.

EXAMPLE 57

4-Methyl-N-[4-[4-[(4-chlorophenyl)thiazol-2-yl]phenoxy]butyl]benzenesulfonamide

A solution of 1.5 g of 2-bromo-1-(4-chlorophenyl)ethanone and 2.5 g of 4-methyl-N-[4-[4-(thiocarbamylphenoxy]butyl]benzenesulfonamide Example 55) in 100 ml of ethanol is stirred at reflux for 17 hours. Cooling the solution gives a precipitate which is collected, washed with ethanol and dried. The precipitate is slurried in 200 ml of saturated NaHCO$_3$ solution for 30 minutes. The insolubles are collected, washed with water, and dried. Recrystallization from ethanol gives the pure compound, m.p. 158°–159° C.; yield, 2.2 g.

EXAMPLE 58

2-[4-(4-Phenylphenoxy)butyl]-1H-isoindole-1,3(2H)-dione

The subject compound is prepared by the procedure of Example 33, 4-phenylphenol replacing the 4-nitrophenol. The resulting solid is collected, m.p. 110°–111° C.

EXAMPLE 59

4-(4-Phenylphenoxy)butaneamine

The title compound is prepared essentially by the procedure of Example 34, 2-[4-(4-phenylphenoxy)-butyl]-1H-isoindole-1,3(2H)-dione (Example 58) replacing the 2-[4-(4-nitrophenoxy)butyl]-1H-isoindole-1,3(2H)-dione. The crude isolated hydrochloride salt has the expected molecular weight as shown by mass spectrometry, and is utilized directly in further synthesis.

EXAMPLE 60

4-Methyl-N-[4-(4-(phenylphenoxy)butyl]benzenesulfonamide

The subject compound is prepared essentially by the procedure of Example 35, 4-(4-phenylphenoxy)butaneamine hydrochloride replacing the 4-[4-nitrophenoxy)butaneanine hydrochloride. After recrystallization from 50% aqueous ethanol, the pure compound is obtained as a solid, m.p. 119°–120° C.

EXAMPLE 61

2-[4-(4-Phenylcarbonylphenoxy)butyl]-1H-isoindole-1,3(2H)-dione

The subject compound is prepared essentially by the procedure of Example 33, (4-hydroxyphenyl)

phenylmethanone replacing the 4-nitrophenol. Recrystallization of the crude product from methanol gives white crystals, m.p. at 53°–55° C.

EXAMPLE 62

4-[(4-Phenylcarbonylphenoxy]butaneamine

The hydrochloride salt of the title compound is prepared essentially by the procedure of Example 34, 2-[4-(4-phenylcarbonyl-phenoxy)butyl]-1H-isoindole-1,3(2H)-dione (Example 61) replacing the 2-[4-(4-nitrophenoxy)butyl]-1H-isoindole-1,3(2H)-dione. The resulting solid is collected, m.p. 188°–190° C.

EXAMPLE 63

4-Bromo-N-[4-(4-phenylcarbonylphenoxy)butyl]benzenesulfonamide

To a solution of 2.0 g of 4-[(4-phenylcarbonylphenoxy]butaneamine hydrochloride (example 62) in a mixture of 40 ml of pyridine and 3 ml of triethylamine is added 2.0 g of 4-bromobenzenesulfonyl chloride. The reaction mixture is stirred at room temperature for 18 hours, heated on the steam bath for one hour, and then added to 250 ml of water. Cooling at 0° C. gives an oil which is dissolved in 100 ml of dichloromethane. Addition of 150 ml of hexane is followed by concentration to turbidity (steam bath), and the mixture cooled at –10° C. An oily solid is precipitated and fine white crystals are produced in the supernatant solvent. These are carefully separated and dried; m.p. 71°–73° C.; recovery, 0.2 g.

EXAMPLE 64

3-Chloro-N-[4-(4-phenylcarbonylphenoxy)butyl]benzenesulfonamide

The tide compound is prepared essentially by the procedure of Example 53 with 3-chlorophenylsulfonyl chloride replacing the 4-methylphenylsulfonyl chloride to give the desired product.

EXAMPLE 65

2-[10-[4-(1H-Imidazol-1-yl)phenoxy]decyl]-1H-isoindole-1,3(2H)-dione

The title compound is prepared essentially by the procedure of Example 1, 2-(10-bromodecyl)-1H-isoindole-1,3(2H)-dione replacing the 4bromobutyl intermediate. After recrystallization from dichloromethane-hexane, the desired compound is collected, m.p. 90°–91° C.

EXAMPLE 66

10-[4-(1H-Imidazol-1-yl)phenoxy]decaneamine

2-[10-[4-(1H-imidazol-1-yl)phenoxy]decyl]-1H-isoindole-1,3(2H)-dione (Example 65) is converted to the free amino derivative by treatment with hydrazine in a refluxing ethanol solution. A portion is converted to its dihydrochloride salt by treatment with concentrated hydrochloric acid in ethanol to give the desired compound, m.p. 190°–192° C. The free base is obtained by treatment with excess 10N NaOH.

EXAMPLE 67

N-[10-[4-(1H-Imidazol-1-yl)phenoxy]decyl]-2-naphthalenesulfonamide

A suspension of 2.5 g of 10-[4-(1H-imidazol-1-yl)phenoxy]decaneamine (Example 66) in 250 ml of diethyl ether containing 3 ml of triethylamine is stirred while 2.0 g of 2-naphthalenesulfonylchloride is added. The reaction mixture is stirred at room temperature for 72 hours and 50 ml of H₂O added. The solvents are decanted, leaving a viscous solid. The solid is dissolved in 100 ml of 50% aqueous ethanol. Careful concentration under a gentle stream of air gives a crystalline solid. The solid is collected washed with water and dried in vacuo at room temperature; m.p. 112°–115° C.; yield, 0.2 g.

EXAMPLE 68

4-Methyl-N-[4-(4-methanesulfonamido)phenyloxy)butyl]benzenesulfonamide

A solution of 3.2 g of 4-methyl-N-[4-(4-aminophenyloxy)butyl]benzenesulfonamide (Example 36) in 50 ml of pyridine is stirred and treated with 1.5 g of methanesulfonyl chloride. The reaction mixture is stirred and heated on the steam bath for 4 hours, and then taken to dryness in vacuo. The residue is stirred with 50 ml of water and acidified to pH <2 with concentrated hydrochloric acid. The precipitate is collected, washed with water, and air dried. Recrystallization from 50% aqueous ethanol, followed by cooling at –10° C. gives 2.0 g of the desired compound, m.p. 121°–122° C. Concentration of the mother liquor gives an additional 0.4 g of product.

EXAMPLE 69

2-[4-(4-Acetamido)phenylthio]butyl-1H-isoindole-1,32-(2H)-dione

To a solution of 5.6 g of 95% sodium methoxide in 400 ml of ethanol is added 16.7 g of 4-acetaniido-benzenethiol and the mixture stirred at room temperature for 15 minutes while 28.2 g of 2-(4-bromobutyl)-1H-isoindole-1,3(2H)-dione is added. The reaction mixture is stirred and heated under reflux for 6 hours and 100 ml of water added. The solution is concentrated to about a 250 ml volume, and stirred at room temperature overnight. The precipitate present is collected, washed with water and air dried. Recrystallization from 50% aqueous ethanol gives the desired product, m.p. 113°–114° C.; yield 33.0 g.

EXAMPLE 70

4-[4-(Acetaindo)phenylthio]butaneamine

To a solution of 26.0 g of 2-[4-(4-acetamidophenylthio)butyl]-1H-isoindole-1,3(2H)-dione (Example 69) in 500 ml of boiling ethanol is added 4 ml of anhydrous hydrazine and refluxing continued for 20 hours. After cooling to room temperature, the precipitate present is collected and washed with 100 ml of ethanol. The ethanolic filtrate is taken to dryness in vacuo. The viscous oily residue is shaken with 200 ml of 1N hydrochloric acid and the insolubles are filtered off. The filtrate is rendered alkaline with 10N sodium hydroxide to give an oil which crystallizes when the mixture is cooled to 0° C. The crystals are collected, washed with cold water, and air dried; yield, 13.3 g. Mass spectroscopy of the product gives a molecular weight of 238, consistent with that expected for 4-[4-(acetamidophenylthio]butaneamine. Treatment with concentrated hydrochloride in ethanol solution gives the hydrochloride salt, m.p. 167°–169° C.

EXAMPLE 71

4-Methyl-N-[4-[4-(acetamido)phenylthio]butyl]benzenesulfonamide

To a solution of 7.2 g of 4-[4-(acetamido)phenylthio]butaneamine (Example 70) in 100 ml of dichloromethane containing 8 ml of triethylamine is added 6.2 g of 4-methylbenzenesulfonyl chloride. The mixture is then stirred under reflux for six hours. The solvents are removed in vacuo. The residue is triturated with 2 portions of 100 ml of water. The insoluble portion is recrystallized from aqueous ethanol. Initially, the product precipitates as an oil, but after standing, crystals are obtained, m.p. 104°–105° C.; yield, 6.6 g.

EXAMPLE 72

4-Methyl-N-[4-(4-ainnophenylthio)butyl]benzenesulfonamide

A mixture of 5.3 g of 4methyl-N-[4-(4-acetamidophenylthio)butyl]benzenesulfonamide, (Example 71) 25 ml of concentrated hydrochloric acid, and 100 ml of ethanol are combined and stirred under reflux for 20 hours. The reaction mixture is taken to dryness in vacuo. The residue is shaken with 200 ml of water and rendered alkaline to pH>14 with 10N sodium hydroxide. The resultant precipitate is collected, washed with water, and dried, 140°–142° C.; yield 2.8 g.

EXAMPLE 73

4-Methyl-N-[4-(4-methanesulfonamidophenylthio)butyl]benzenesulfonamide

A solution of 2.4 g of 4-methyl-N-[4-(4-aminophenylthio)butyl]benzenesulfonamide (Example 72) in 50 ml of pyridine is treated with 1.05 g of methane-sulfonyl chloride, and the solution stirred and heated on the steam bath for 6 hours. The pyridine is then removed in vacuo. The residue is shaken with 100 ml of water, and the mixture acidified below pH=2 with concentrated hydrochloric acid. The precipitate is collected, washed with water and dried. Recrystallization from 50% aqueous ethanol gives shiny white crystals after drying, m.p. 95°–96° C.; yield, 1.2 g.

EXAMPLE 74

4-Methyl-N-[4-(4-acetamidophenylsulfonyl)butyl]benzenesulfonamide

A solution of 2.0 g of 4-methyl-N-[4-(4-acetamidophenylthio)butyl]benzenesulfonamide (Example 71) in 100 ml of acetic acid is heated at 90°–95° C. After addition of 10 ml of 30% hydrogen peroxide, the mixture is stirred at steam bath temperature for 16 hours. Dilution with 300 ml of cold water produces an oily precipitate which is collected on a diatomaceous earth filter pad. Extraction of the filter pad with 250 ml of boiling acetone, followed by concentration to dryness in vacuo gives an oily residue. Recrystallization from 50% aqueous ethanol gives the desired compound, m.p. 93°–95° C.; yield, 0.3 g.

EXAMPLE 75

4-Methyl-N-[4-[4-(pyrrol-1-yl)phenyloxy]butyl]benzenesulfonamide

A mixture of 3.2 g of 4-methyl-N-[4-(4-aminophenyloxy)butyl]benzenesulfonamide (Example 36), 1.5 g of 2,5-dimethoxytetrahydrofuran, and 50 ml of acetic acid is stirred and heated on the steam bath for 16 hours. The reaction mixture is taken to dryness in vacuo. The residue is shaken with 150 ml of dichloromethane and 150 ml of saturated sodium bicarbonate solution. The dichloromethane layer is separated, dried over $Na_2SO_4$, and diluted with 100 ml of hexane. The solution is concentrated until turbid, then cooled at −10° C. The precipitate that forms is collected, washed with hexane, and air dried; m.p. 124°–126° C.; yield, 0.2 g.

EXAMPLE 76

4-Chloro-N-[4-[4-(1H-imidazol-1-yl)phenyloxy]butyl]benzamide

A solution of 2.8 g of 4-[4-(1H-imidazol-1-yl)phenoxy]butylamine hydrochloride (Example 2) in 50 ml of water is treated successively with 4 ml of 10N NaOH and 2.0 g of 4-chlorobenzoyl chloride in 100 ml of diethyl ether. Stirring at room temperature for 3 hours gives a precipitate which is collected, washed with diethylether and water, and air dried. Recrystallization from 33% aqueous ethanol gives the desired product, m.p. 138°–139° C.; yield, 1.3 g.

EXAMPLE 77

4-Bromo-N-[4-[4-(1H-imidazol-1-yl)phenoxy]butyl]benzamide

The tide compound is prepared essentially by the procedure of Example 76, 4-bromobenzoyl chloride replacing the 4-chlorobenzoyl chloride; m.p. 140°–141° C.

EXAMPLE 78

2-Bromo-N-[4-[4-(1H-imidazol-1-yl)phenoxy]butyl]benzamide

The title compound is prepared by the procedure of Example 76, 2-bromobenzoyl chloride replacing the 4-chlorobenzoyl chloride. Recrystallization from 50% aqueous methanol gives the desired product, m.p. 138°–139° C.

EXAMPLE 79

N-[4-[4-(1H-Imidazol-1-yl)phenoxy]butyl]benzamide

The title compound is prepared by the procedure of Example 76, benzoyl chloride replacing the 4-chlorobenzoyl chloride. After recrystallization from 33% aqueous ethanol, the compound has m.p. of 117°–118° C.

EXAMPLE 80

4-Methyl-N-[4-[4-(1H-imidazol-1-yl)phenoxy]butyl]benzamide

4-[4-(1H-Imidazol-1-yl)phenoxy]butaneamine dihydrochloride (Example 2) is treated with 10N NaOH (mixture pH >12). The oil present is extracted with dichloromethane. Removal of the dichloromethane in vacuo gives the 4-[4-(1H-imidazol-1-yl)phenoxy]butanearnine as a viscous oil which is used directly for further synthesis. A solution of 2.3 g of 4-[4-(1H-imidazol-1-yl)phenoxy]butaneamine in 25 ml of pyridine is treated with 1.8 g of 4-methylbenzoyl chloride. After heating at steam bath temperature for one hour, the reaction mixture is added to 400 ml of water precipitating a viscous oil. The aqueous phase is decanted. A solution of the oil in 200 ml of hot 50% aqueous methanol, followed by cooling at −10° C. gives a tacky precipitate, but a white crystalline precipitate develops in the supernatant solvent. The crystals are carefully collected, washed with cold $H_2O$ and dried in vacuo at room temperature, m.p. 128°–130° C.; yield, 0.7 g.

EXAMPLE 81

4-Methoxy-N-[4-[4-(1H-imidazol-1-yl)phenoxy]butyl]benzamide

A solution of 2.3 g of 4-[4-(1H-imidazol-1-yl)phenoxy] butaneamine (Example 2) in 50 ml of dichloromethane containing 2 ml of pyridine is treated with 2.0 g of 4-methoxybenzoyl chloride. The reaction mixture is allowed to stand at room temperature for 18 hours, and is then heated at reflux for one hour. The volatiles are removed in vacuo. The residue is partitioned between 100 ml of dichloromethane and 100 ml of water. The dichloromethane layer is dried over $Na_2SO_4$, and then heated to gentle boiling. Hexane is then added to turbidity and the mixture cooled at $-10°$ C. A tacky precipitate results and crystals develop in the supernatant solvent. These are collected, washed with hexane, and dried in vacuo at room temperature; m.p. 125°–126° C.; yield, 0.4 g.

EXAMPLE 82

N-[4-[4-(1H-Imidazol-1-yl)phenoxy]butyl]-1-naphthalenecarboxamide.

The preparation of the title compound is carried out essentially in the procedure of Example 81, 1-naphthoyl chlorine replacing the 4-methoxybenzoylchloride. After removal of the volatiles, the residue is treated with 100 ml of 1N NaOH and 100 ml of diethyl ether, and mixture then cooled at 0° C. overnight. The precipitate is collected and recrystallized from 50% aqueous ethanol and dried; m.p.157°–159° C.

EXAMPLE 83

4-Fluoro-N-[4-[4-(1H-imidazol-1-yl)phenoxy]butyl]benzamide

The title compound is prepared essentially by the procedure of Example 81, 4-fluorobenzoyl chloride replacing the 4-methoxybenzoylchloride. The crude product is recrystallized from diethyl ether and dried m.p. 122°–123° C.

EXAMPLE 84

4-Iodo-N-[4-[4-(1H-imidazol-1-yl)phenoxy]butyl]benzamide

The title compound is prepared essentially by the procedure of Example 76, 4-iodobenzoyl chloride replacing the 4-chlorobenzoyl chloride. The pure compound is obtained after recrystallization from 50% aqueous ethanol, m.p. 143°–145° C.

EXAMPLE 85

N-(4-Bromophenyl)-N'-[4-[4-(1H-imidazol-1-yl)phenoxy]butyl]urea

Solutions of 4-[(4-(imidazol-1-yl)-phenoxy]-butaneamine (Example 2) in diethyl ether (1.6 g in 400 ml) and 4-bromophenylisocyanate in diethyl ether (1.4 g in 100 ml) are mixed. A white precipitate forms immediately. After 30 minutes, the title compound is collected, washed with diethyl ether, and dried m.p. 157°–159° C.; yield, 1.7 g.

EXAMPLE 86

4-Bromo-N-[5-[4-(1H-imidazol-1-yl)phenoxy]pentyl]benzamide

A solution of 2.9 g of 5-[4-(1H-imidazol-1-yl)phenoxy]pentaneamine (Example 27) in 150 ml of dichloromethane and 100 ml 1N NaOH are combined and stirred vigorously as 2.8 g of 4-bromobenzoyl chloride is added. The reaction mixture is stirred at room temperature for 20 hours, the dichloromethane layer separated and dried over $Na_2SO_4$. The dichloromethane solution is diluted with 200 ml of hexane, and the solution concentrated to turbidity. Cooling the mixture at room temperature gives the desired product as white crystals, m.p. 150°–151° C.; yield, 1.4 g.

EXAMPLE 87

O,O'-Diphenyl-N-[4-[4-(1H-imidazol-1-yl)phenyloxy]butyl]phosphoramide

A solution of 3.0 grams of 4-[4-(1H-imidazol-1-yl)phenoxy]butaneamine hydrochloride (Example 2) in 100 ml of water is stirred and treated with 3.3 ml of 10N sodium hydroxide. A solution of 2.9 g of O,O', diphenylphosphoryl chloride in 100 ml of diethyl ether is added, and the mixture stirred at room temperature for six hours. The diethyl ether is removed in a stream of air, leaving a viscous solid in the aqueous phase. The mixture is cooled to 0° C., and the water decanted. The solid is dissolved in 100 ml of ethyl acetate and the solution then dried over $Na_2SO_4$. The ethyl acetate solution is cooled to 0° C. and diluted with 300 ml of hexane. Cooling at $-10°$ C. leads to the formation of a precipitate which is collected, washed with hexane, and dried in vacuo at 40° C. to give 1.5 g of the title compound, m.p. 110°–112° C.

EXAMPLE 88

P,P-Diphenyl-N-[4-[4-(1H-imidazol-1-yl)phenoxy]butyl]phosphinamide

A mixture consisting of 3.0 g of 4-[4-(1H-imidazol-1-yl)phenoxy]butanearine dihydrochloride (Example 2) is triturated with 3.5 ml of 10N sodium hydroxide. To the mixture is added 150 ml of methylene chloride followed by 20 g of sodium sulfate. After stirring for 25 minutes, the solids are removed by filtration. To the filtrate are added, with stirring, 3 ml of triethylamine and then 2 ml of diphenylphosphinic chloride. The reaction mixture is stirred at room temperature for 2 hours, washed with 100 ml of water and dried over sodium sulfate. Removal of the methylene chloride in vacuo leaves a viscous oil which crystallizes on stirling with 25 ml of diethyl ether. The precipitate is collected, washed with 75 ml of diethyl ether, and dried in vacuo at room temperature. The melting pointis 106°–107° C.

EXAMPLE 89

N-[4-[4-(1H-Tetrazol-1-yl)phenoxy]butyl]-2,1,3-benzothiadiazole-4-sulfonamide

A mixture consisting of 0.9 g of 4-[4(1H-tetrazol-1-yl)phenoxy]butaneamine hydrochloride (Example 39) and 1 ml of 10N sodium hydroxide is stirred until all solid has disappeared. The suspension is stirred with 150 ml of dichloromethane and 7 g of anhydrous sodium sulfate for 30 minutes. The insolubles are removed by filtration. The filtrate is then treated with 1.5 ml of triethylamine followed by a solution of 0.93 g of 2,1,3-benzothiadiazole-4-sulfonyl chloride in 25 ml of dichloromethane. The reaction mixture is stirred at room temperature for 16 hours. It is then washed with an equal volume of water. After drying with anhydrous $Na_2SO_4$, the dichloromethane is removed in vacuo, leaving a yellow solid. Recrystallization from a mixture of dichloromethane/diethyl ether gives 0.7 g of pure product, m.p. 142°–143° C.

EXAMPLE 90

3-Bromo-N-[4-[4-(1H-imidazol-1-yl)phenoxy]butyl] benzamide

The title compound is prepared by the procedure of Example 76, 3-bromobenzoyl chloride replacing the 4-chlorobenzoyl chloride. Recrystallization from methanol gives the desired product, m.p. 89°–91° C.

EXAMPLE 91

2-[3-[4-(1H-Imidazol-1-yl)phenoxy]proply]-1H-isoindole-1,3(2H)-dione

To 100 ml of absolute ethyl alcohol is added 1.01 g of sodium followed by stirring for 30 minutes and adding 10.7 g of N-(3-bromopropyl)phthalimide. After refluxing for 4 hours, the mixture is cooled to room temperature, methylene chloride added and filtered to remove insolubles. The filtrate is dried ($MgSO_4$) and evaporated in vacuo to give 13.5 g of residue. A sample is crystallized from ethyl alcohol to give tan solid, m.p. 113°–117° C.

EXAMPLE 92

3-[4-(1H-Imidazol-1-yl)phenoxy]propanamine

A mixture of 17.0 g of 2-[3-[4-(1H-imidazol-1-yl)phenoxy]propyl]-1H-isoindole-1,3(2H)-dione (Example 91) and 2.8 ml of hydrazine hydrate in 150 ml of ethyl alcohol is refluxed for 3 hours. The reaction mixture is cooled and 225 ml of 3N HCl added followed by refluxing for 2 hours and standing at room temperature for 18 hours. The reaction mixture is filtered and the filtrate evaporated in vacuo to a residue which is washed with ethyl alcohol and ether, dried in a vacuum oven to give 12.0 g of the dihydrochloride salt of the title compound as a tan solid, m.p. 208°–220° C.

EXAMPLE 93

4-Bromo-N-[3-[4-(1H-imidazol-1-yl)phenoxy] propyl]benzamide

A mixture of 2.04 g of 3-[4-(1H-imidazol-1-yl)phenoxy] propanamine dihydrochloride (Example 92) in 70 ml of methylene chloride is treated with 21 ml of 1N NaOH followed by 1.54 g of 4-bromobenzoyl chloride with stirring at room temperature for 18 hours. Additional methylene chloride and 5 ml of 1N NaOH is added and the organic layer separated, washed with water and filtered. The organic layer is evaporated in vacuo to a residue which is washed with ether and dried to give 1.3 g of off-white solid, m.p. 183°–185° C.

EXAMPLE 94

N-[4-[3-(1,3-Dihydro-1,3-dioxo-2H-isoindol-2-yl) propoxy]phenyl]acetamide

To a solution of 15.1 g of 4-acetanidophenol is 150 ml of N,N-dimethylformamide is added 4.0 g of 60% sodium hydride in mineral oil followed by stirring until gas evolution ceases. A 26.8 g portion of N-(3-bromopropyl) phthalimide is added and the reaction mixture heated on a steam bath for 16 hours. The reaction mixture is poured into 1 liter of cold water and the resulting solid collected and washed with 1 liter of cold water and the solid vacuum dried. A 5 g sample is crystallized from 25 ml of ethanol to give 1.5 g of solid, m.p. 155°–157° C. The remaining sample is crystallized from ethanol to give 23.4 g of solid, m.p. 154°–156° C.

EXAMPLE 95

2-[3-(4-Aminophenoxy)propyl]-1H-isoindole-1,3 (2H)-dione

A solution of 10.0 g of N-[4-[3-(1,3-dihydro-1,3-dioxo-2H-isoindol-2-yl)propoxy]phenyl]acetamide (Example 94) in 500 ml of ethanol is treated with 100 ml of HCl and refluxed for 8 hours and allowed to stand at room temperature for 18 hours. The precipitate is collected, washed with 50 ml of ethanol and air dried to give 8.6 g of solid as the hydrochloride salt. A 1.5 g sample is crystallized from ethanol: water to give 1.2 g of the HCl salt of the title compound, m.p. 250°–260° C.

EXAMPLE 96

N-[4-[3-(1,3-Dihydro-1,3-dioxo-2H-isoindol-2-yl) propoxy]phenyl]methanesulfonamide A 7.0 g sample of 2-[3-(4-aminophenoxy)-propyl]-1H-isoindole-1,3(2H)-dione monohydrochloride (Example 95) is added to 100 ml of pyridine, 2.2 ml of 10N NaOH and 2.5 g methanesulfonyl chloride. The mixture is stirred at room temperature for 6 hours and 1 hour on a steam bath. The reaction mixture is poured into 900 ml of cold water and stored at 0° C. for 18 hours. The precipitate is collected, washed with 200 ml of water and dried to give 6.5 g of solid. A 1.0 g sample is crystallized from 100 ml of boiling ethanol after treatment with activated carbon to give 0.6 g of solid, m.p. 176°–178° C.

EXAMPLE 97

3-[4-(Methanesulfonylamino)phenoxy] propaneamine

A suspension of 5.5 g of N-[4-[3-(1,3-dihydro-1,3-dioxo-2H-isoindol-2-yl)propoxy]phenyl]methanesulfonamide in 200 ml of ethanol is treated with 1.5 ml of hydrazine hydrate and the mixture stirred and refluxed for 6 hours. A precipitate forms in 1 hour. After 6 hours, 5 ml of HCl is added and the mixture refluxed for 1 hour and allowed to stand at room temperature for 18 hours. The precipitate is collected, stirred with 50 ml of hot water and the insolubles washed with 50 ml of water. The combined water washes are evaporated in vacuo to a dry residue. The residue is dissolved in 100 ml of saturated sodium bicarbonate, treated with activated carbon, filtered and the filtrate acidified with acetic acid and concentrated in vacuo to 100 ml. The precipitate is collected, washed with 25 ml of cold water and dried to give a solid, m.p. 200° C.

EXAMPLE 98

4-Bromo-N-[3-[4-(methylsulfonylamino)phenoxy] propyl]benzamide

A 1.6 g sample of Example 97, 4-[4-(methanesulfonylamino)-phenoxy]propaneamine is dissolved in 50 ml of water and 3 ml of 100N NaOH. While stirring, a solution of 1.7 g of 4-bromobenzoyl chloride in 100 ml of diethyl ether is added. After stirring for 5 hours, a precipitate forms and 2 ml of acetic acid is added. The precipitate is collected, washed with 50 ml of water and air dried to a residue(A). The filtrate is air evaporated to a residue(B). Residue A is crystallized from ethanol:water to give 1.1 g of solid, m.p. 209°–210° C. Residue B is crystallized from ethanol: water to give 0.4 g of solid, m.p. 208°–209° C.

EXAMPLE 99

4Methyl-N-[4-[4-(1H-imidazol-1-yl)phenoxy]-2-butyn-1-yl]benzenesulfonamide

Following the procedures of Examples 30, 31, and 32 and substituting 1,4-dichloro-2-butyne for (E)-1,4-dichloro-2-butene in the procedure of example 30, the title compound is obtained.

PHARMACOLOGY

1. Action Potential Duration Prolongation Test Description

Preparation of Cardiac Muscle

Male Hartley guinea-pigs (Charles River, N.Y.) weighing between 120 and 160 grams are anesthetized intraperitoneally with Pentothal. After thoracotomy, the heart is removed and immediately placed in oxygenated (100% $O_2$) Tyrode's-HEPES solution of the following composition: NaCl 140.0 mM, KCl 4.0 mM, $MgCl_2$ 1.0 mM, $CaCl_2$ 1.8 mM, Glucose 10.0 mM, and HEPES pH 7.4, 5.0 mM. Thin (less than 1 mm) papillary muscle is excised from the right ventricle and mounted in a 1.5 ml plexiglas chamber (BSC chamber, Medical Systems Corp., Greenvale, N.Y.). The chamber is constantly perfused at a rate of 2.5 ml/min. with oxygenated Tyrode's-HEPES solution at a constant temperature of 37° C.

Measurements of transmembrane action potentials

The stimulating and recording electronics is assembled from Digitimer Neurolog modules (Medical Systems Corp., Greenvale, N.Y.). The isolated papillary muscle is held in place by a bipolar platinum stimulating electrode, which is connected to a Neurolog NL800 Stimulus Isolation Unit. The pair of platinum wires is insulated with teflon except at the tips, and the interelectrode distance is less than 1 mm. Electrical stimulation of the muscle is done with pulses of 1 millisecond in duration delivered from a Neurolog NL510 Pulse Buffer according to signals generated by Neurolog NL304 Period Generator and NL403 Delay-Width units. The stimulus threshold is determined during experiments before drug perfusion and the intensity of the current pulse is set 1.5 times the threshold. The preparation is paced at 0.5 Hz for at least 1 hour for equilibration before measurements are made. Transmembrane action potentials are intracellularly recorded with 3M KCl-filled glass capillary microelectrodes (Dagan Corp., Minneapolis, Minn.), with tip diameters <1 $\mu$m and impedances of 20–50 Meghoms. A single impalement is maintained throughout control and drug-superfusing periods. A silver-silver chloride electrode in the bath serves as reference. Signals are amplified with Neurolog NL102 DC PreAmp and NL106 AC-DC Amplifier and displayed on a Tektronix 5110 oscilloscope. Action potentials are plotted on- line by a Hewlett-Packard 7475-A plotter. Signals are also fed to DATA 6100 Universal Waveform Analyzer (Data Precision, Danvers, Mass.) for on-line analyses of action potential waveforms. Experimental timing signals, initialization of DATA 6100, acquisition of analyzed data from DATA 6100, and plotting functions are under the control of custom software which is run on an IBM-AT microcomputer. Action potential parameters computed with DATA 6100 are: maximum upstroke velocity (max dV/dT), action potential amplitude (APA), resting membrane potential (RMP), and action potential duration at 25% (APD25), 50% (APD50), and 90% (APD90) repolarization.

The current series of compounds produced a minimum of 5% increase in action potential duration prolongation using the test conditions described above.

2. Significance of Data

Class III anti-arrhythmic agents prolong the cardiac action potential duration by blocking cardiac potassium channels. This prolongation of the action potential duration causes a prolongation of cardiac tissue refractoriness, namely, a delay in the recovery of tissue from inexcitability. When a re-entrant impulse meets an inexcitable tissue, the impulse is terminated and the arrhythmia disappears. Agents capable of eliciting this effect would be useful in circumventing sudden death due to ventricular tachycardia and fibrillation, the most lethal cardiac disorder which kills almost half a million Americans annually.

Class III anti-arrhythmic agents may also be effective against atrial fibrillation, a condition that afflicts millions of elderly. One unique feature of this class of compounds is the lack of excessive prolongation of the cardiac action potential at slow rhythms. This finding suggests that the compounds would show lesser proarrhythmic tendencies, particularly the type known as "Torsades de Pointes." The existing anti-arrhythmic agents show this pro-arrhythmic tendency.

As potassium channel blockers, the compounds can find other usefulness as memory-enhancers in Alzheimer's disease, neurotransmitter release in depression and insulin release in diabetes.

TABLE I

| EXAMPLE NO. | % ACTION POTENTIAL DURATION (APD) 10 $\mu$M Drug 60 Min |
|---|---|
| 3 | 18.2 |
| 4 | 19.9 |
| 5 | 2.4 |
| 6 | 8 |
| 7 | 35.6 |
| 9 | 11.4 |
| 10 | 23.1 |
| 10 | 16.6 |
| 11 | 16.6 |
| 12 | 12.9 |
| 13 | 9.4 |
| 14 | 13.6 |
| 15 | 28.7 |
| 16 | 7.8 |
| 17 | 18.7 |
| 18 | 11.6 |
| 19 | 6.6 |
| 22 | 14.5 |
| 24 | 7.3 |
| 25 | 4 |
| 28 | 22.2 |
| 32 | 23.4 |
| 36 | 3.2 |
| 40 | 27.6 |
| 41 | 17.5 |
| 44 | 3.4 |
| 47 | 13.3 |
| 50 | 3.5 |
| 53 | 11.2 |
| 67 | 9.1 |
| 68 | 7.4 |
| 76 | −1.3 |
| 77 | 10.1 |
| 78 | 6.7 |
| 83 | 11.5 |
| 84 | 11.3 |
| 86 | 2.5 |
| 87 | 14.3 |
| 90 | 9.6 |
| 93 | 4.3 |
| 98 | 5.3 |

When the compounds, or where applicable as a pharmaceutically acceptable salt, are ties, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage fonns suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of phannaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

In particular, the antiairhythmlc compounds of this invention are therapeutically useful in the treatment and as a viable therapeutic strategy for the management of ventricular arrhythmias and the prevention of sudden cardiac death.

What is claimed is:

1. A compound according to Formula I:

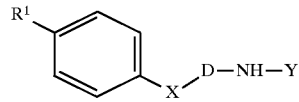

FORMULA I wherein $R^1$ is

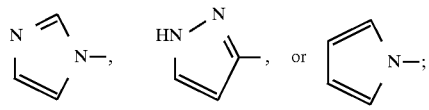

X is O, S, SO, or $SO_2$;

D is $-(CH_2)_n-$, cis or trans $-(CH_2)_k-CH=CH-(CH_2)_m-$, or $-(CH_2)_k-C\equiv C-(CH_2)_m-$, where n is 3–10, m is 1–4, and k is 1–4;

Y is $C(=O)R^2$ or $SO_2R^2$;

$R^2$ is

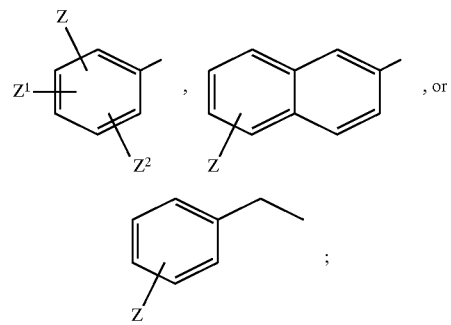

Z, $Z^1$ and $Z^2$ are independently selected from H, $C_1$–$C_4$ straight or branched alkyl, $-CF_3$, $-NO_2$, $-NHCOR^3$, $-OR^4$, $-CN$, Cl, Br, F, or I;

$R^3$ is $C_1$–$C_3$ straight chain alkyl; and $R^4$ is a $C_{1-C4}$ straight or branched alkyl;

with the provisos that when $R^1$ is 1-imidazolyl, X is oxygen, D is $-(CH_2)_4-$, Y is $-C(=O)R^2$, $R^2$ is

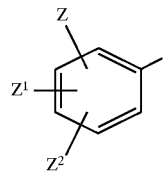

and two of Z, $Z^1$ and $Z^2$ are H, then the remaining substituent Z, $Z^1$, or $Z^2$ cannot be Cl in the 4-position; and when $R^1$ is 1-imidazolyl, D is $-(CH_2)_n-$ Y is $-SO_2R^2$ and $R^2$ is

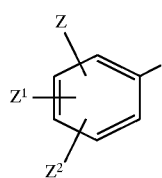

at least one of Z, Z$^1$ and Z$^2$ is selected from CF$_3$, —NO$_2$, —NHCOR$^3$, and —CN; or a pharmaceutically acceptable salt thereof.

2. A compound according to claim 1 wherein Y is C(=O)R$^2$.

3. A compound according to claim 1 selected from:

N-[4-[4-(1H-imidazol-1-yl)phenoxy]butyl]-2-naphthalenesulfonamide,

N-[4-[4-(1H-imidazol-1-yl)phenoxy]butyl]benzenemethanesulfonamide, 4-trifluoromethyl-N-[4-[4-(1H-imidazol-1-yl) phenoxy]butyl]benzene sulfonamide, 4-acetamido-N-[4-[4-(1H-imnidazol-1-yl)phenoxy]butyl] benzenesulfonamnide, 4-cyano-N-[4-[4-(1H-imnidazol-1-yl)phenoxy]butyl] benzenesulfonamide, N-[10-[4-[(1H-imnidazol-1-yl)phenoxy]decyl]]-2-naphthalenesulfonamide, 4-bromo-N-[4-[4-(1H-pyrazol-3-yl)phenoxy]butyl] benzenesulfonamide, 4-methyl-N-[4-(pyrrol-1-yl)phenyloxy]butyl] benzenesulfonamnide, 4-Bromo-N-[4-[4-(1H-imidazol-1-ylphenoxy]butyl] benzamide, 2-Bromo-N-[4-[4-(1H-inmidazol-1-yl)phenoxy]butyl] benzamide, N-[4-[4-(1H-Imidazol-1-yl)phenoxy]butyl]benzamide, 4-Methyl-N-[4-[4-(1H-imidazol-1-yl)phenoxy]butyl] benzamide, 4-Methoxy-N-[4-[4-(1H-imidazol-1-yl)phenoxy]butyl] benzarnide, N-[4-[4-(1H-Imidazol-1-yl)phenoxy]butyl]-1-naphthalenecarboxamide, 4-Fluoro-N-[4-[4-(1H-imidazol-1-yl)phenoxy]butyl] benzamide, 4-Iodo-N-[4-[4-(1H-imidazol-1-yl)phenoxy]butyl] benzamnide, and 3-Bromo-N-[4-[4-(1H-imidazol-1-yl)phenoxy]butyl] benzamide or a pharmaceutical salt thereof.

4. A method of treating cardiac arrhythmias in a mammal which comprises administering to a mammal having a cardiac arrhythrnia a therapeutically effective amount of a compound according to Formula I:

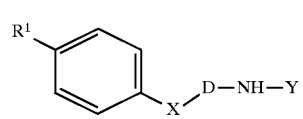

FORMULA I wherein

R$^1$ is

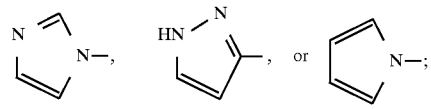

X is O, S, SO, or SO$_2$;

D is —(CH$_2$)$_n$—, cis or trans —(CH$_2$)$_k$—CH=CH—(CH$_2$)$_m$—, or —(CH$_2$)$_k$—C≡C—(CH$_2$)$_m$—, where n is 3–10, m is 1–4, and k is 1–4;

Y is C(=O)—R$^2$ or SO$_2$R$^2$;

R$^2$ is

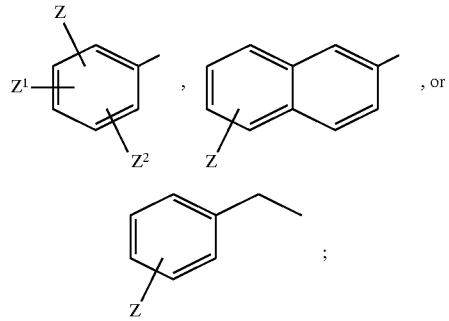

Z, Z$^1$ and Z$^2$ are independently selected from H, C$_1$–C$_4$ straight or branched alkyl, —CF$_3$, —NO$_2$, —NHCOR$^3$, —OR$^4$, —CN, Cl, Br, F, or I;

R$^3$ is C$_1$–C$_3$ straight chain alkyl; and

R$^4$ is a C$_1$–C$_4$ straight or branched alkyl;

with the proviso that when R$^1$ is 1-imidazolyl, X is oxygen, D is —(CH$_2$)$_4$—, Y is C(=O)R$^2$, R$^2$ is

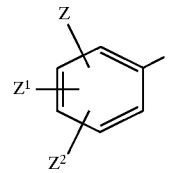

and two of Z, Z$^1$ and Z$^2$ are H, then the remaining substituent Z, Z$^1$, or Z$^2$ cannot be Cl in the 4-position; or a pharmaceutically acceptable salt thereof.

5. A compound according to claim 1 which is 4-nitro-N-[4-[4-(1H-imidazol-1-yl)phenoxy]butyl] benzenesulfonamide.

6. A compound according to claim 1 which is (E)-4-methyl-N-[4-[4-(1H-imidazol-1-yl)phenoxy]-2-buten-1yl] benzenesulfonamide.

7. A compound according to claim 1 wherein R$^1$ is imidazolyl or tetrazolyl, X is O, Y is —SO$_2$R$^2$, R$^2$ is phenyl substituted by Z, Z$^1$, and Z$^2$ or R$^2$ is 8-quinolinyl, and D, Z, Z$^1$, Z$^2$, and R$^3$ and R$^4$ are as defined in claim 1.

8. A compound according to claim 1 where R$^1$ is imidazol-1-yl, X is O, D is butylene, and Y is —COR$^2$.

9. A pharmaceutical composition comprising a pharmaceutically acceptable carrier and a therapeutically effective amount of a compound according to claim 1.

* * * * *